United States Patent
Aoyama

(10) Patent No.: US 10,222,954 B2
(45) Date of Patent: Mar. 5, 2019

(54) IMAGE DISPLAY APPARATUS, DISPLAY CONTROL APPARATUS AND DISPLAY CONTROL METHOD USING THUMBNAIL IMAGES

(71) Applicant: CANON KABUSHIKI KAISHA, Tokyo (JP)

(72) Inventor: Gakuto Aoyama, Kyoto (JP)

(73) Assignee: CANON KABUSHIKI KAISHA, Tokyo (JP)

(*) Notice: Subject to any disclaimer, the term of this patent is extended or adjusted under 35 U.S.C. 154(b) by 476 days.

(21) Appl. No.: 14/736,335

(22) Filed: Jun. 11, 2015

(65) Prior Publication Data

US 2015/0363053 A1 Dec. 17, 2015

(30) Foreign Application Priority Data

Jun. 11, 2014 (JP) .................. 2014-120582
Jun. 11, 2014 (JP) .................. 2014-120844

(51) Int. Cl.
*G06F 3/0484* (2013.01)
*G06F 3/0481* (2013.01)
(Continued)

(52) U.S. Cl.
CPC .......... *G06F 3/04842* (2013.01); *A61B 6/463* (2013.01); *A61B 8/463* (2013.01);
(Continued)

(58) Field of Classification Search
CPC .......... G06T 2219/028; H04N 1/00442; H04N 1/00453; H04N 1/00461; H04N 21/4312;
(Continued)

(56) References Cited

U.S. PATENT DOCUMENTS 6,785,410 B2 8/2004 Vining et al.
7,058,901 B1* 6/2006 Hafey ................. G06F 19/3406
345/619
(Continued)

FOREIGN PATENT DOCUMENTS

CN 1719446 A 1/2006
CN 101053521 A 10/2007
(Continued)

OTHER PUBLICATIONS

Office Action issued in Chinese Patent Application No. 201510319870.X dated Sep. 1, 2017. English translation provided.
(Continued)

*Primary Examiner* — Nicholas Ulrich
(74) *Attorney, Agent, or Firm* — Rossi, Kimms & McDowell LLP

(57) ABSTRACT

A display control apparatus for displaying medical image data generates a thumbnail for selecting medical image data, using a reduced image obtained from the medical image data. In the thumbnail, partial areas are set according to anatomical areas obtained from the medical image data. In response to an instruction to select the thumbnail that is displayed, the display control apparatus displays a medical image corresponding to the thumbnail. The display control unit determines a display content of the medical image that is to be displayed on the display unit, based on a designated position in the thumbnail in the instruction.

23 Claims, 22 Drawing Sheets

| PARTIAL AREA | ANATOMICAL AREA |
|---|---|
| PARTIAL AREA 122 | SOFT REGION |
| PARTIAL AREA 123 | LUNG-FIELD REGION |
| PARTIAL AREA 124 | BONE REGION |
| : | : |

(51) Int. Cl.
*A61B 6/00* (2006.01)
*A61B 8/00* (2006.01)
*H04N 21/4728* (2011.01)
*H04N 21/4725* (2011.01)
*G16H 30/40* (2018.01)
*G16H 30/20* (2018.01)
*G06F 3/0482* (2013.01)
*G06F 19/00* (2018.01)

(52) U.S. Cl.
CPC .......... *G06F 3/0482* (2013.01); *G06F 3/0484* (2013.01); *G06F 3/04817* (2013.01); *G06F 19/00* (2013.01); *G06F 19/321* (2013.01); *G16H 30/20* (2018.01); *G16H 30/40* (2018.01); *H04N 21/4725* (2013.01); *H04N 21/4728* (2013.01)

(58) Field of Classification Search
CPC ............ H04N 21/4725; H04N 21/4728; G06F 19/32; G06F 19/327; G06F 19/34; G06F 19/3487; G06F 19/322; G06F 19/3443; G06F 19/345; G06F 3/0484; G06F 19/321; G06F 3/04842; G06F 3/04845; G06F 3/04886; G06F 2203/04806; G06F 2203/04803; G06F 3/04817; A61B 6/463; A61B 1/00045; A61B 6/465; A61B 8/463
See application file for complete search history.

(56) References Cited

U.S. PATENT DOCUMENTS

| | | | |
|---|---|---|---|
| 7,683,909 B2 | 3/2010 | Takekoshi | |
| 8,312,374 B2* | 11/2012 | Ozawa | G06F 17/30277 345/157 |
| 8,634,611 B2 | 1/2014 | Minakuchi et al. | |
| 8,731,263 B2* | 5/2014 | Fukatsu | G06F 19/321 382/128 |
| 8,913,078 B2* | 12/2014 | Masumoto | G06F 19/321 345/619 |
| 8,971,601 B2 | 3/2015 | Zaiki et al. | |
| 9,019,301 B2 | 4/2015 | Matsue et al. | |
| 9,122,773 B2 | 9/2015 | Li et al. | |
| 9,262,444 B2* | 2/2016 | Gross | G06F 17/30274 |
| 2003/0071829 A1* | 4/2003 | Bodicker | G06F 17/30274 345/619 |
| 2007/0065044 A1* | 3/2007 | Park | G06F 17/30247 382/305 |
| 2007/0242069 A1* | 10/2007 | Matsue | G06F 19/321 345/428 |
| 2008/0294974 A1* | 11/2008 | Nurmi | G06F 17/30905 715/204 |
| 2010/0131890 A1* | 5/2010 | Natanzon | G06F 3/0481 715/808 |
| 2011/0028825 A1 | 2/2011 | Douglas et al. | |
| 2011/0149147 A1* | 6/2011 | Oh | H04N 9/8042 348/441 |
| 2014/0341450 A1* | 11/2014 | Sedan | H04N 19/132 382/128 |

FOREIGN PATENT DOCUMENTS

| | | |
|---|---|---|
| CN | 101398742 A | 4/2009 |
| CN | 101645111 A | 2/2010 |
| CN | 101662584 A | 3/2010 |
| CN | 102596035 A | 7/2012 |
| CN | 102609175 A | 7/2012 |
| CN | 103198499 A | 7/2013 |
| EP | 2533543 A2 | 12/2012 |
| JP | 2005510326 A | 4/2005 |
| JP | 2007029248 A | 2/2007 |
| JP | 2008077210 A | 4/2008 |
| JP | 2009070074 A | 4/2009 |
| JP | 2011130433 A | 6/2011 |
| JP | 2011217947 A | 11/2011 |
| JP | 2012000472 A | 1/2012 |
| JP | 2012081180 A | 4/2012 |
| JP | 2012247879 A | 12/2012 |
| JP | 2012247880 A | 12/2012 |
| JP | 2013152534 A | 8/2013 |
| JP | 2014000475 A | 1/2014 |
| JP | 2014012040 A | 1/2014 |
| JP | 2014012208 A | 1/2014 |
| KR | 1020100071595 A | 6/2010 |
| WO | 2013046940 A1 | 4/2013 |

OTHER PUBLICATIONS

Office Action issued in Chinese Appln. No. 201510312174.6 dated Jan. 19, 2018. English translation provided.
Office Action issued in U.S. Appl. No. 14/736,347 dated Oct. 5, 2017.
Office Action issued in U.S. Appl. No. 14/736,347 dated Apr. 12, 2018.
Notice of Allowance issued in U.S. Appl. No. 14/736,347 dated Oct. 30, 2018.
Office Action issued in Japanese Appln. No. 2014-120582 dated May 22, 2018. English translation provided.
Office Action issued in Japanese Appln. No. 2014-120842 dated Jul. 6, 2018. English machine translation provided.
Office Action issued in Japanese Appln. No. 2014-120582 dated Aug. 14, 2018. English machine translation provided.

* cited by examiner

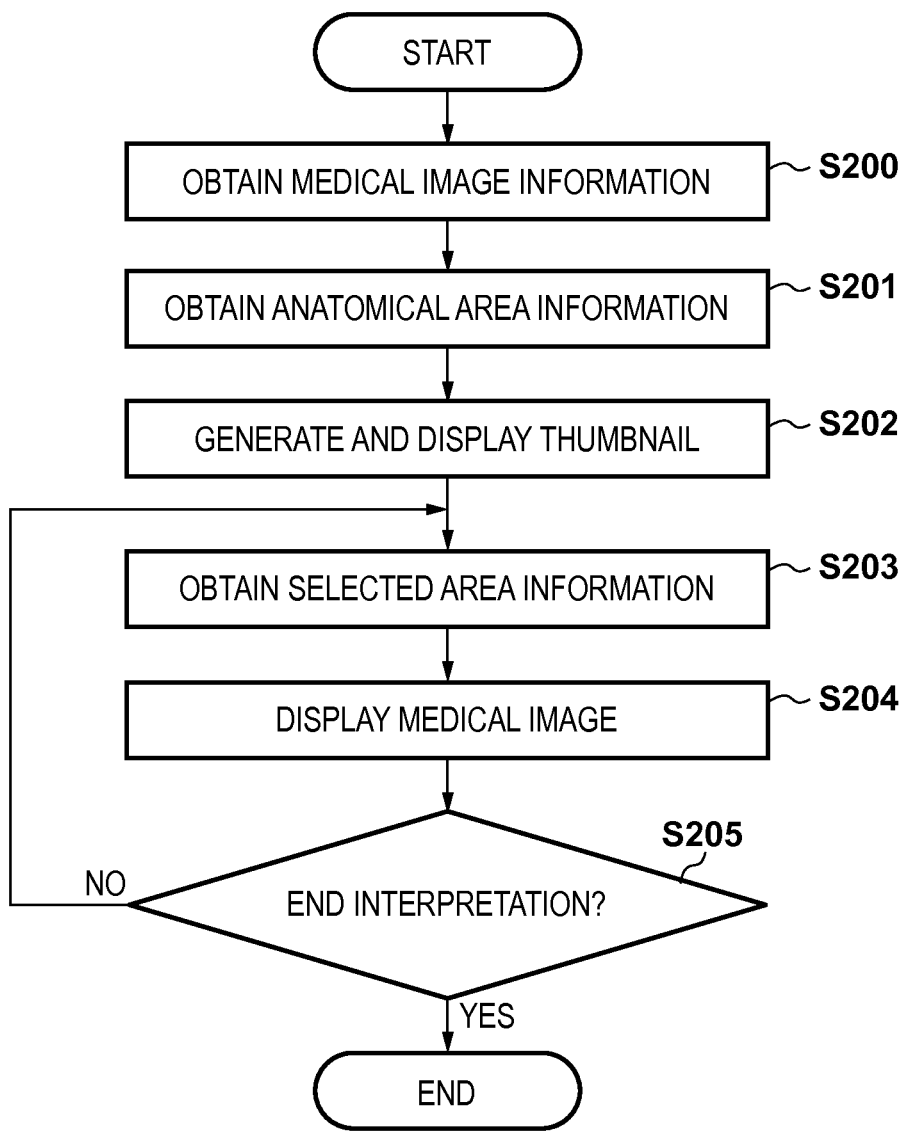

FIG. 3A
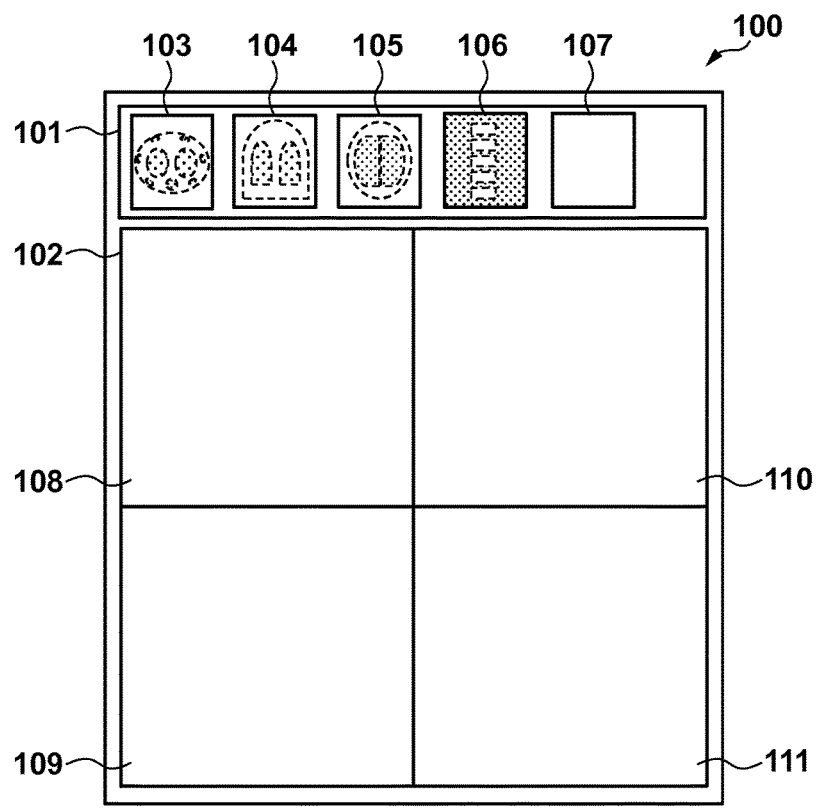
FIG. 3B
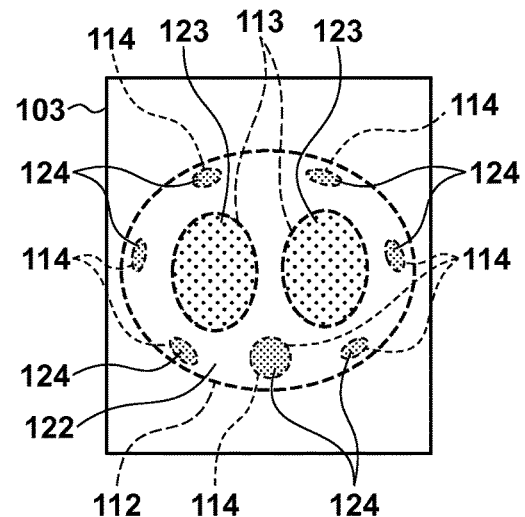
FIG. 3C
| PARTIAL AREA | ANATOMICAL AREA |
|---|---|
| PARTIAL AREA 122 | SOFT REGION |
| PARTIAL AREA 123 | LUNG-FIELD REGION |
| PARTIAL AREA 124 | BONE REGION |
| ⋮ | ⋮ |

F I G. 12A    F I G. 12B
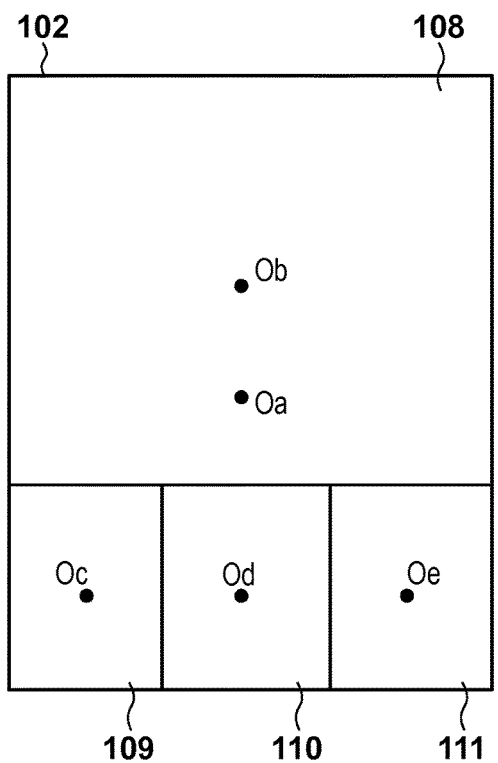
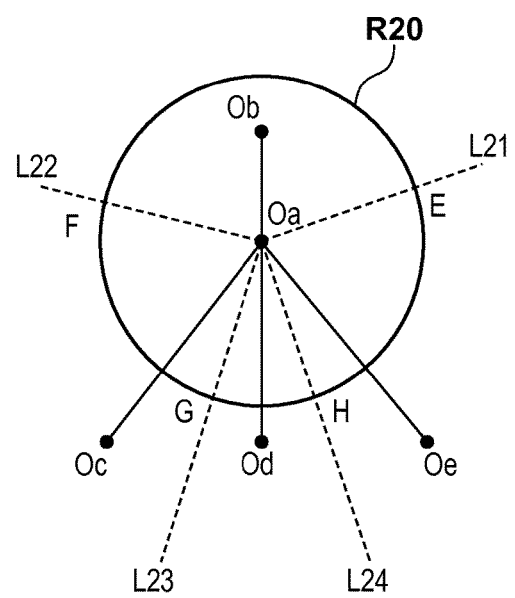

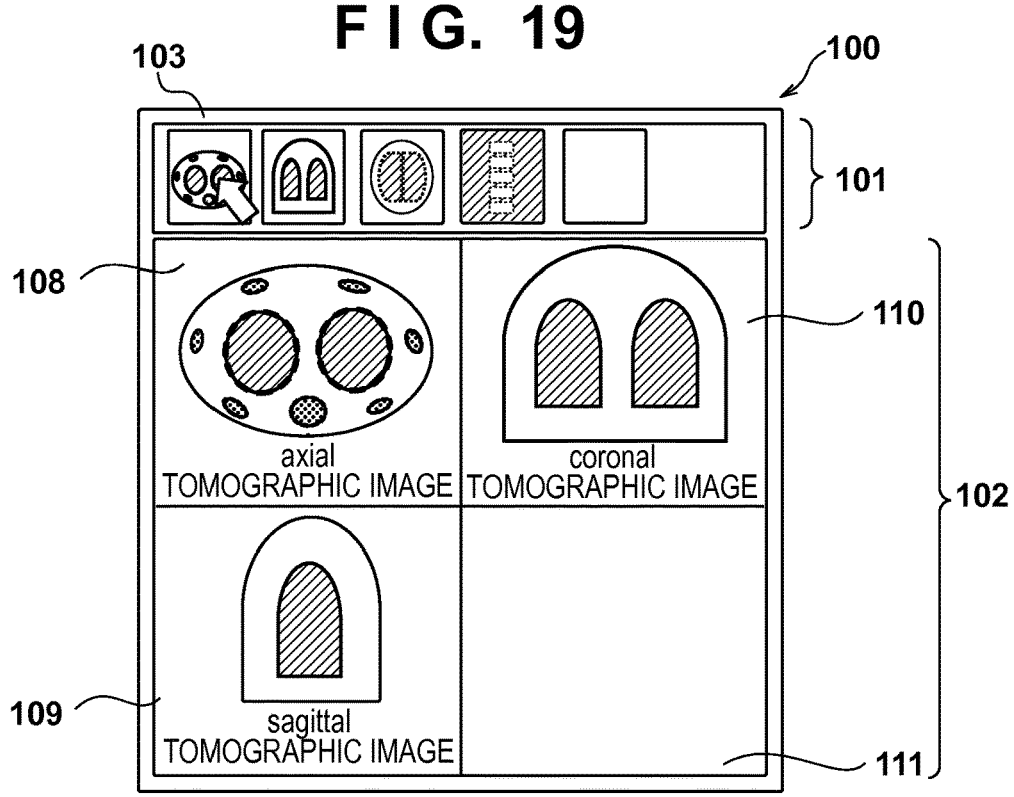
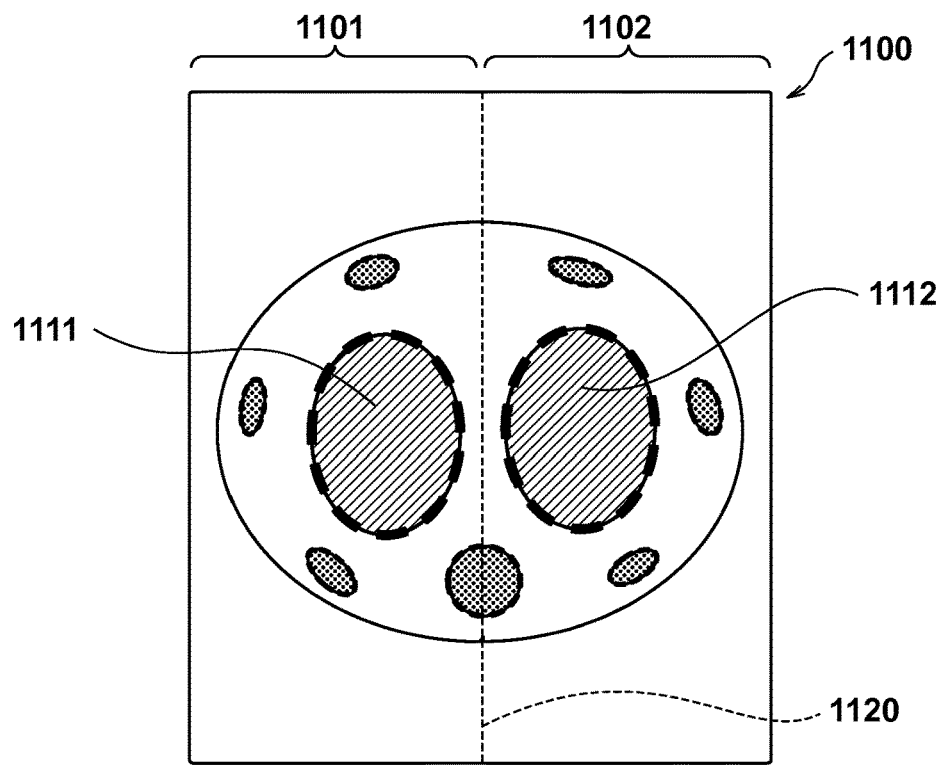

F I G. 24
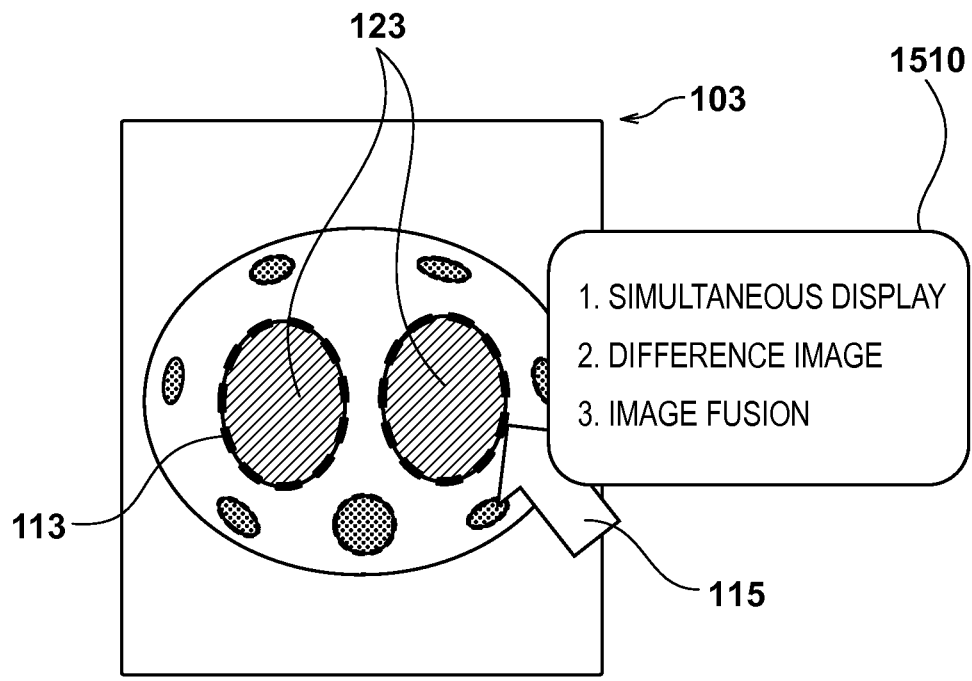

IMAGE DISPLAY APPARATUS, DISPLAY CONTROL APPARATUS AND DISPLAY CONTROL METHOD USING THUMBNAIL IMAGES

BACKGROUND OF THE INVENTION

Field of the Invention

The present invention relates to a display control apparatus and a display control method for medical images, an image display apparatus using the display control apparatus, and a program.

Description of the Related Art

In the medical field, medical image capturing apparatuses such as X-ray computed tomography (CT) apparatuses, magnetic resonance imaging (MRI) apparatuses, and positron emission tomography (PET) apparatuses are used to capture medical images. Medical image data obtained by capturing images is subjected to various types of image processing, and stored for a certain period of time in data servers in hospitals. When making diagnoses with images, doctors use a medical image display apparatus (sometimes referred to as a viewer) to search for target medical image data and display it on a monitor, while using various functions of the medical image display apparatus.

This sort of medical image display apparatus displays a thumbnail image (hereinafter, referred to as a thumbnail) corresponding to a medical image, and, upon accepting selection of the thumbnail by a user, displays the medical image corresponding to the selected thumbnail so that a diagnosis can be made from the medical image. The displayed medical image from which a diagnosis is to be made can be subjected to various functions of the medical image display apparatus, such as an enlargement and reduction function, a density value conversion function, a display position parallel movement function, a graphic drawing function, and a density value measurement function, on the entire image.

Meanwhile, medical image data has different optimum display conditions depending on anatomically classified areas (anatomical areas) even if they are areas displayed in the same image, and, thus, the images are displayed with their display condition being changed by a user according to an area that is to be observed, and are subjected to interpretation. For example, the user can change the display condition, using a known density value conversion function in the medical image display apparatus. The density value conversion function is a function of converting each pixel value in the gray scale according to a predetermined rule. Typically, a CT image is expressed in a Hounsfield unit (HU) value in 12-bit tones (4,096 tones) per pixel, and this HU value is stored as a pixel value. When a doctor observes a CT image, two density conversion parameters consisting of window level (WL) and window width (WW) as defined in the DICOM standard are used to convert a 12-bit tone pixel value (HU value) into an 8-bit tone value, and the image is displayed on a display screen. Accordingly, it is possible to easily see a difference in HU values (density difference) in a specific organ or tissue. Also in images (MRI images, PET images, ultrasonic images, etc.) other than CT images, density conversion as described above is performed in order to make it possible to easily see a difference in pixel values (density difference). More specifically, when observing in detail a lung-field region in a CT image showing a breast region, the WL is set to −600, and the WW is set to 1500. When observing in detail a mediastinal region in a CT image showing a breast region, the WL is set to 60, and the WW is set to 400. When observing in detail a bone region in a CT image showing a breast region, the WL is set to 500, and the WW is set to 2500.

Japanese Patent Laid-Open No. 2011-217947 (hereinafter, referred to as Document 1) describes a technique in which, when a freely selected area is designated in three-dimensional data, an image display condition is changed. With this technique, a CT image can be efficiently displayed in a display condition corresponding to a designated area, and, thus, the user effort can be reduced.

However, typically, a thumbnail is merely for specifying a corresponding medical image, and, thus, after a medical image corresponding to a selected thumbnail is displayed, the display condition has to be changed using the technique as shown in Document 1. Accordingly, there is a problem that it requires effort to perform interpretation.

SUMMARY OF THE INVENTION

An embodiment of the present invention provides an image display apparatus, a display control apparatus, a display control method, and a program that make it possible to display freely selected medical image data, in a display condition suitable for an area that is to be observed, with a simple operation.

According to one aspect of the present invention, there is provided a display control apparatus for displaying medical image data, comprising: a generation unit configured to generate a thumbnail for selecting medical image data, using a reduced image obtained from the medical image data; and a display control unit configured to display a medical image corresponding to the thumbnail, on a display unit, in response to an instruction to select the thumbnail that is displayed, wherein the display control unit determines a display content of the medical image that is to be displayed on the display unit, based on a designated position in the thumbnail in the instruction.

According to another aspect of the present invention, there is provided an image display apparatus, comprising: the above-described display control apparatus; and a display unit configured to display the thumbnail and the medical image data.

According to another aspect of the present invention, there is provided a display control apparatus, comprising: a display processing unit configured to display a reduced image of a main image which is representative of a data set including a plurality of medical images, on a display unit; an acceptance unit configured to accept a selection instruction on a partial area that is set in the reduced image; and a specifying unit configured to specify the medical image corresponding to the partial area according to the selection instruction, wherein the display processing unit further displays the medical image specified by the specifying unit.

According to another aspect of the present invention, there is provided a display control method for a display control apparatus, comprising: a generation step of generating a thumbnail for selecting medical image data, using a reduced image obtained from the medical image data; and a display control step of displaying a medical image corresponding to the thumbnail, on a display unit, in response to an instruction to select the thumbnail that is displayed; wherein, in the display control step, a display content of the medical image that is to be displayed on the display unit is determined based on a designated position in the thumbnail in the instruction.

Further features of the present invention will become apparent from the following description of exemplary embodiments with reference to the attached drawings.

BRIEF DESCRIPTION OF THE DRAWINGS

FIG. 2 is a flowchart illustrating the overall processing of the first embodiment.

FIGS. 3A and 3B are diagrams showing a screen configuration example according to the first embodiment.

FIG. 3C is a diagram illustrating management of association between partial areas and anatomical areas.

FIGS. 12A and 12B are diagrams illustrating a relationship between the input range of directional information and the partial display area selected.

FIG. 19 is a diagram showing a display screen according to a third modified example.

FIG. 20 is a diagram showing an exemplary thumbnail according to a fifth modified example.

FIG. 24 is a diagram showing a display example of an image processing selection window.

DESCRIPTION OF THE EMBODIMENTS

Hereinafter, some embodiments of the present invention will be described with reference to the appended drawings. Note that the scope of the invention is not limited to these examples.

First Embodiment

Figure 1:
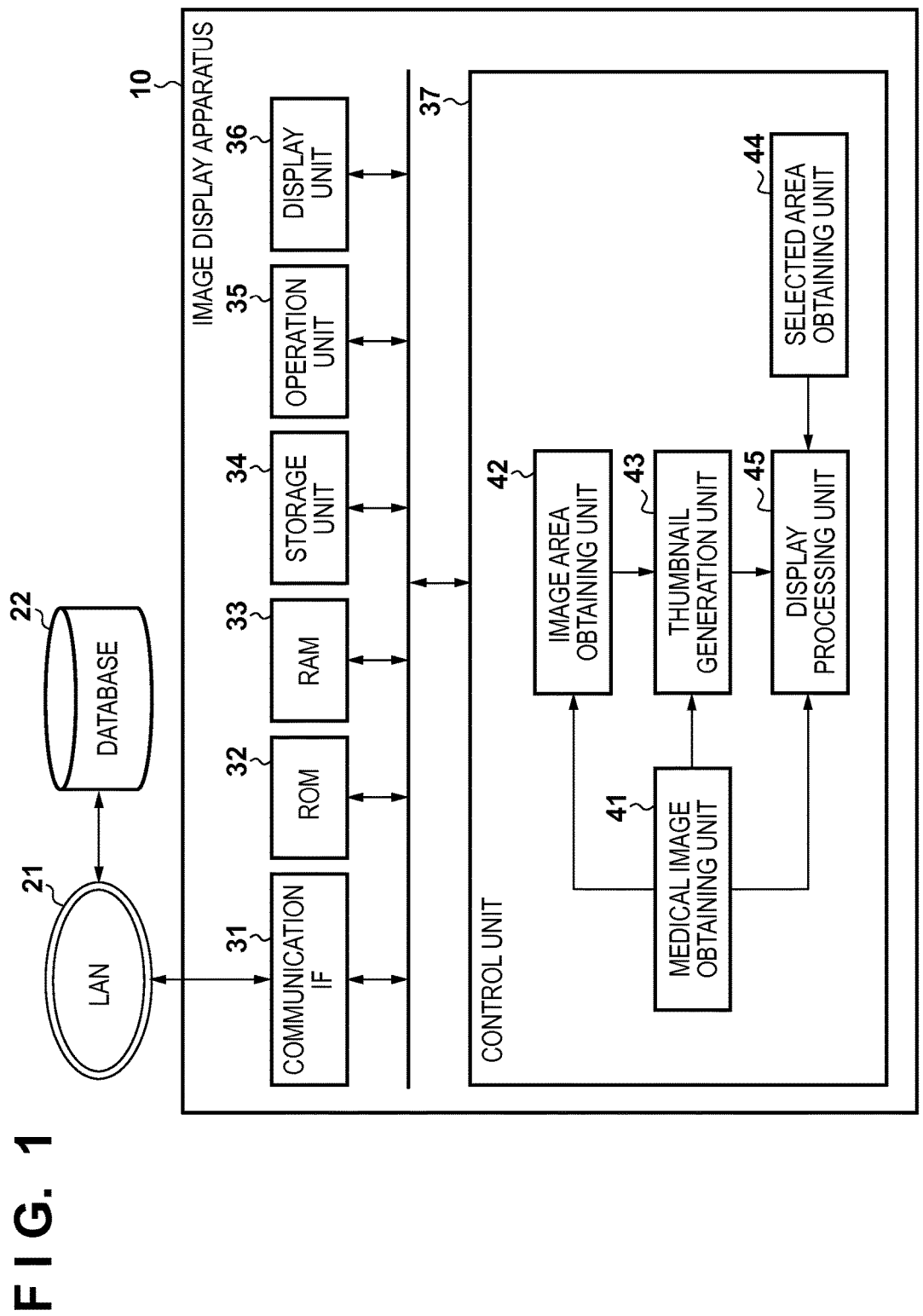
FIG. 1 is a block diagram of a medical image display system according to a first embodiment.

FIG. 1 is a diagram showing the overall configuration of a medical image display system according to the first embodiment. The medical image display system includes an image display apparatus 10 for displaying medical image data and a database 22 for storing medical image data, and these apparatuses are communicably connected to each other. In this embodiment, the image display apparatus 10 and the database 22 communicate with each other using a local area network (LAN) 21. The database 22 manages examination information such as medical image data, and the image display apparatus 10 obtains and displays medical image data managed in the database 22, via the LAN 21.

The image display apparatus 10 has a communication interface (IF) 31, a read only memory (ROM) 32, a random access memory (RAM) 33, a storage unit 34, an operation unit 35, a display unit 36, and a control unit 37. The communication IF 31 is realized by a LAN card or the like, and is used for communication between an external apparatus (e.g., the database 22) and the image display apparatus 10 via the LAN 21. The ROM 32 is realized by a nonvolatile memory or the like, and stores various programs and the like. The RAM 33 is realized by a volatile memory or the like, and temporarily stores various types of information. The storage unit 34 is realized by a hard disk drive (HDD) or the like, and stores various types of information. The operation unit 35 is realized by a keyboard, a mouse, or the like, and is used to input instructions from a user to the apparatus. The display unit 36 is realized by a display screen or the like, and displays various types of information to a user (e.g., a doctor).

The control unit 37, which is an exemplary display control apparatus for controlling display of medical image data, is realized by a central processing unit (CPU) or the like, and performs comprehensive control of the processing in the image display apparatus 10. The control unit 37 has a functional configuration including a medical image obtaining unit 41, an image area obtaining unit 42, a thumbnail generation unit 43, a selected area obtaining unit 44, and a display processing unit 45.

The medical image obtaining unit 41 obtains medical image data via the communication IF 31 and the LAN 21 from the database 22, and outputs it to the image area obtaining unit 42, the thumbnail generation unit 43, and the display processing unit 45. The image area obtaining unit 42 performs image processing (described later) on the medical image data obtained from the medical image obtaining unit 41, determines anatomically classified areas (hereinafter, referred to as anatomical areas) in the medical image data, obtains area information thereof, and outputs the information to the thumbnail generation unit 43.

The thumbnail generation unit 43 generates a thumbnail, using a reduced image of the medical image data showing a disease condition obtained by the medical image obtaining unit 41 and information on the anatomical areas in the medical image data obtained by the image area obtaining unit 42, and outputs the thumbnail to the display processing unit 45. The selected area obtaining unit 44 obtains selected area information of an area selected via the operation unit 35 by the user in the thumbnail displayed on the display unit 36, and outputs it to the display processing unit 45. The display processing unit 45 displays the thumbnail generated by the thumbnail generation unit 43, on the display unit 36. The display processing unit 45 further displays the medical image data showing a disease condition obtained from the medical image obtaining unit 41, on a main display area (e.g., a main display area 102 in FIG. 3A) of the display unit 36, according to the selected area information obtained by the selected area obtaining unit 44.

Note that at least part of the units included in the control unit 37 may be realized by an independent apparatus. Furthermore, each unit may be realized by software for realizing the function. In this embodiment, it is assumed that each unit is realized by software.

Figure 4A:
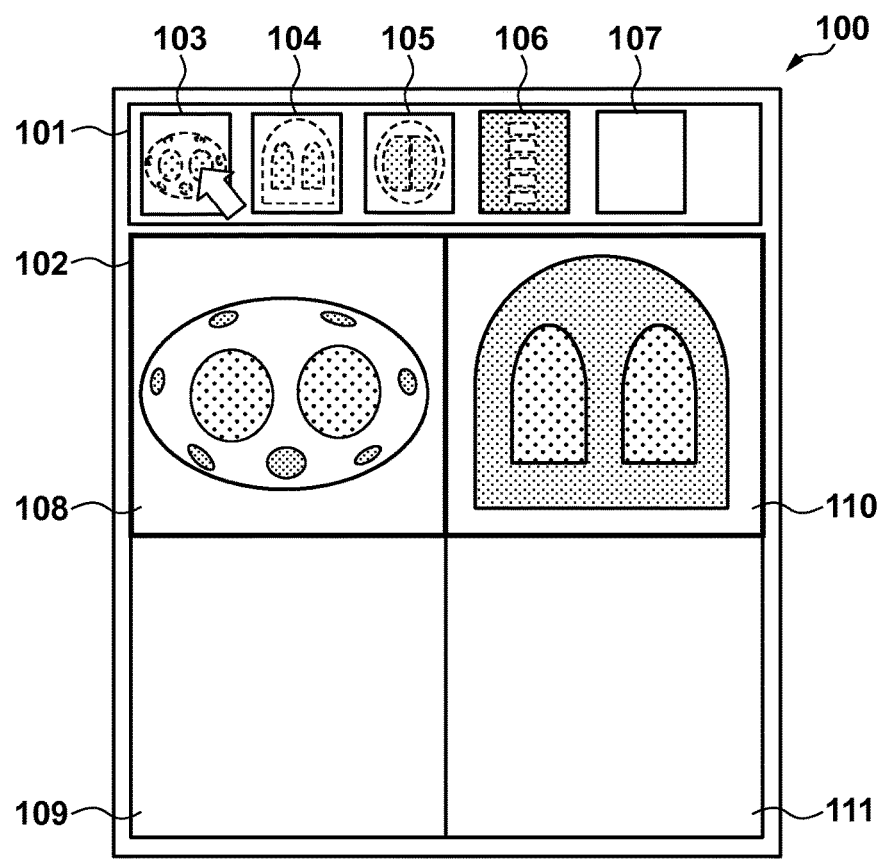
FIGS. 4A to 4C are diagrams showing a screen configuration example when a divided area in a thumbnail is selected.
Figure 4B:
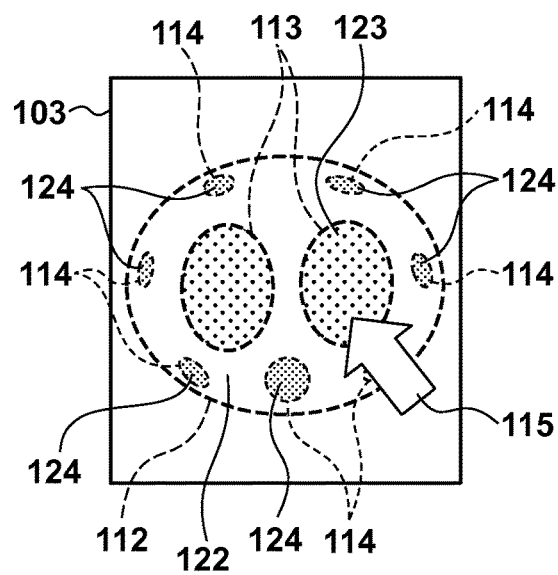
Figure 4C:
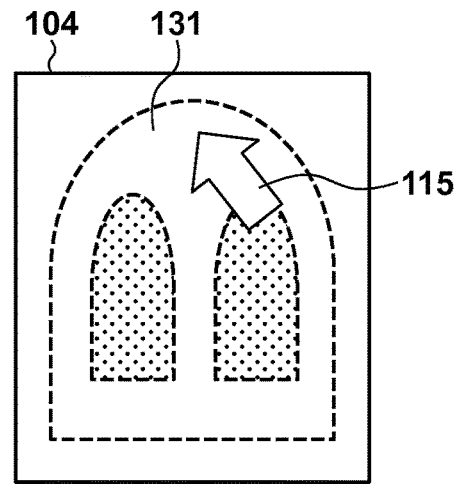

Next, the overall processing by the control unit 37 in this embodiment will be described with reference to FIGS. 2, 3A to 3C, and 4A to 4C. FIG. 2 is a flowchart illustrating the processing performed by the control unit 37. FIGS. 3A and 4A show exemplary screens displayed on the display unit 36 through the processing (described later). FIGS. 3B, 4B and 4C show enlarged views of thumbnails 103 and 104 shown in FIGS. 3A and 4A.

In FIGS. 3A and 4A, a thumbnail display area 101 on a display screen 100 displays, for example, a thumbnail of at least one medical image previously or currently captured from one patient. Thumbnails 103 to 107 show display examples of thumbnails generated by the thumbnail generation unit 43 from a medical image. A main display area 102 is an area for displaying medical image data corresponding to the selected thumbnail, that is, a medical image selected as data on which interpretation is to be performed by a user. The medical image displayed in the main display area 102 can be subjected to various functions of the image display apparatus, such as an enlargement and reduction function, a density value conversion function, a display position parallel movement function, a graphic drawing function, and a density value measurement function, on the entire image. The main display area 102 is divided into a plurality of partial display areas for displaying medical image data. In this embodiment, the main display area 102 is divided into four partial display areas 108 to 111. If a desired thumbnail is dragged and dropped onto a desired partial display area, medical image data corresponding to the thumbnail is displayed in the partial display area onto which the thumbnail was dropped. Hereinafter, medical image data that is an X-ray CT image of a breast region will be described as an example, but it will be appreciated that medical image data to which the present invention can be applied is not limited to this.

In the flowchart shown in FIG. 2, in step S200, the medical image obtaining unit 41 reads medical image data via the communication IF 31 and the LAN 21 from the database 22. In step S201, the image area obtaining unit 42 extracts anatomical areas from the medical image data read in step S200, and obtains area information thereof. Anatomical areas are extracted, for example, as follows.

First, the image area obtaining unit 42 performs noise removal using a smoothing filter on the medical image data. Next, binarization processing is performed using a predetermined threshold (e.g., HU value: −200) with respect to an image pixel value, so that a region inside the body and a region outside the body are separated from each other. Furthermore, the area inside the body is separated into a bone region and the other region, using another threshold (e.g., HU value: 300). Furthermore, the other region is separated into a lung-field region and a soft region, using another threshold (e.g., HU value: −500). Note that processing for extracting anatomical areas may be any processing as long as predetermined areas can be extracted from the read medical image data, and there is no limitation to this method. For example, anatomical areas may be extracted using known organ segmentation processing such as graph cut processing. Regarding the areas that are to be extracted, for example, correspondence between image information obtained from a Digital Imaging and Communications in Medicine (DICOM) header or the like and areas that are to be extracted is set in advance as shown in Table 1, and extraction areas corresponding to image information contained in the medical image data are extracted. As shown in Table 1, anatomical areas that are to be extracted from the medical image data are determined based on a modality used to capture the medical image data and an image capture site. The table as shown in Table 1 is stored in the storage unit 34 or the like.

TABLE 1

| Image information | | |
|---|---|---|
| Modality | Image Capture site | Extraction area |
| CT | Breast region | Lung-field, bone, others |
| CT | Abdominal region | Liver, stomach, lung-field, others |
| CT | Head region | Cerebrum, eye, tooth, others |
| MRI | Breast region | Lung-field, bone, others |
| MRI | Abdominal region | Liver, lung-field, others |
| MRI | Head region | Cerebrum, cerebellum, eye, tooth, others |
| PET | All | None |
| Others | All | None |

In step S202, the thumbnail generation unit 43 generates a thumbnail, through the following processing. First, the thumbnail generation unit 43 generates image data corresponding to the medical image data read in step S200 (hereinafter, referred to as corresponding image data). If the read medical image data is two-dimensional medical image data (one slice image), the corresponding image data is that slice image, or an image obtained by extracting part of the slice image. On the other hand, if the read medical image data is three-dimensional medical image data (a plurality of slice images), the corresponding image data is a slice image representative of the three-dimensional medical image data, or a slice image at a predetermined position (e.g., first slice image). Alternatively, the corresponding image data may be an image obtained by extracting part of the slice image. The slice image representative of the three-dimensional medical image data may be a slice image containing all extraction areas determined in advance according to the image information of the medical image data as shown in Table 1, or may be a slice image containing the largest number of types of extraction areas. Subsequently, the thumbnail generation unit 43 generates a reduced image from the corresponding image data, and generates a thumbnail using the generated reduced image.

Next, the thumbnail generation unit 43 extract partial areas from the thumbnail, according to the anatomical areas extracted in step S201. For example, if a region outside the body, a lung-field region, a soft region, and a bone region are obtained in step S201, and these regions are contained in the corresponding image data, the thumbnail generation unit 43 extracts partial areas corresponding to these areas from the reduced image. Then, dividing lines (broken lines in FIG. 3B) showing boundaries between the partial areas are generated such that the extracted partial areas can be seen. Accordingly, a thumbnail is generated in which the dividing lines are drawn or overlaid on the reduced image. In FIG. 3B, a dividing line 112 shows a boundary between a region outside the body and a region inside the body, dividing lines 113 show boundaries between lung-field regions and a soft region, and dividing lines 114 show boundaries between bone regions and a soft region. In this manner, in the thumbnail 103, partial areas 122 to 124 that have been divided along the dividing lines 112 to 114 are set. The thumbnail generation unit 43 sets the partial areas 122 to 124, for example, as shown in FIG. 3B, and manages correspondence between each partial area and an anatomical area as shown in FIG. 3C. The partial areas 122, 123 and 124 are also referred to as soft region 122, lung-field region 123 and bone region 124 respectively.

If there are a plurality of pieces of medical image data read in step S200, the thumbnail generation unit 43 performs this processing on all pieces of medical image data, and generates a thumbnail for all pieces of medical image data. The display processing unit 45 displays the thumbnails generated by the thumbnail generation unit 43 side by side in the thumbnail display area 101. In the example in FIG. 3A, the thumbnails 103 to 107 are displayed in the thumbnail display area 101.

In step S203, the selected area obtaining unit 44 obtains information indicating a partial area in the thumbnail selected by the user using the operation unit 35. For example, if the user clicks on the partial area 123 in the thumbnail 103 using a pointing device (e.g., mouse) that is not shown, the selected area obtaining unit 44 obtains information indicating the partial area 123 that was clicked on. FIGS. 4A to 4C show a screen example on the display unit 36 at the time of this operation. A pointer 115 is a pointer (e.g., a mouse pointer) operated by a pointing device, and indicates a current position of input performed with the operation unit 35.

In step S204, the display processing unit 45 displays the medical image data corresponding to the thumbnail selected in step S203, in the main display area 102, in a display condition suitable for an anatomical area corresponding to the partial area specified at the time of the selection. In the example in FIG. 4B, the partial area 123 (lung-field region) in the thumbnail 103 is selected with the pointer 115, and, for example, medical image data corresponding to the thumbnail 103 is displayed in the partial display area 108 in a display condition suited to observe a lung-field region as shown in FIG. 4A. FIG. 4C shows a state in which the pointer 115 selects the thumbnail 104 and specifies a partial area 131 corresponding to a soft region. In this case, medical image data corresponding to the thumbnail 104 is displayed in the partial display area 110 in the main display area 102 in a display condition suited to observe a soft region.

Note that which partial display area of the plurality of partial display areas (e.g., the partial display areas 108 to 111) is used to display the medical image data corresponding to the selected thumbnail is determined according to a predetermined rule. For example, the state of each partial display area (whether or not currently displaying an image) is obtained, and, if there is a partial display area displaying no image, the medical image data is preferentially displayed in that partial display area. If images have been already displayed in all partial display areas, the medical image data may be always displayed in a determined partial display area (e.g., a partial display area in the leftmost and uppermost position). Alternatively, the medical image data may be displayed in a partial display area in which an image displayed at the earliest point in time is currently displayed. For example, a partial display area for displaying new medical image data may be determined such that the partial display area 108→the partial display area 109→the partial display area 110→the partial display area 111 are repeated in this order. Alternatively, the new medical image data may be displayed in a partial display area in which an image having a record of user operation performed thereon at the earliest point in time is currently displayed. If another piece of medical image data has been already displayed in a partial display area in which the medical image data corresponding to the selected thumbnail is to be displayed, the other piece of medical image data is deleted, after which the corresponding medical image data is displayed.

In step S205, the control unit 37 judges whether or not an instruction to end the interpretation has been received from the user via the operation unit 35. The instruction to end the interpretation is given, for example, by the user clicking on an interpretation end button that is not shown. If an instruction to end the interpretation has been received, the procedure in FIG. 2 is ended. If an instruction to end the interpretation has not been received, the procedure returns to step S203.

As described above, with the image display apparatus according to the first embodiment, the following effects are obtained. That is to say, if any selected partial area in any selected thumbnail is selected, medical image data corresponding to the thumbnail can be displayed in the main display area in a display condition corresponding to the selected partial area. Accordingly, it is possible to provide an image display apparatus and an image display method that require less user effort, because medical image data can be displayed in the main display area in a display condition suited to perform interpretation, with an operation that selects any medical image data.

Modified Example 1

Figure 5:
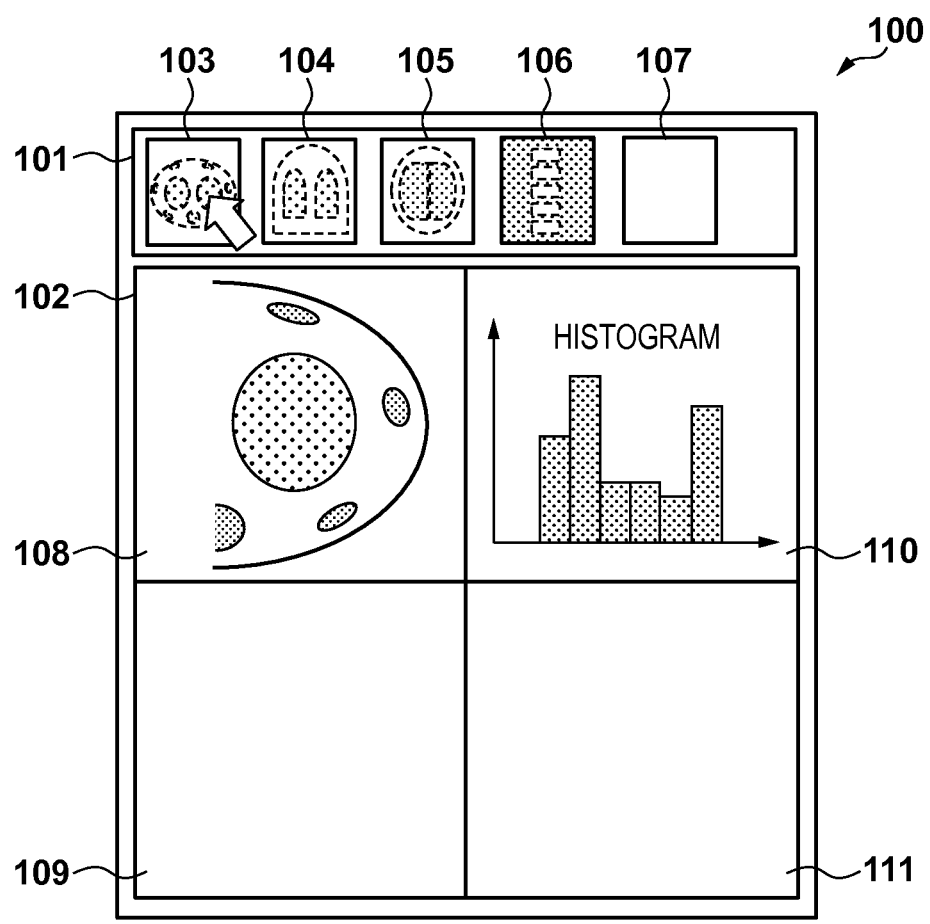
FIG. 5 is a diagram showing a screen configuration example according to Modified Example 1 of the first embodiment.

In this embodiment, an examples was described in which image density values (HU values) are changed (tone conversion) according to a partial area in a thumbnail selected in step S204. However, the display condition subjected to change is not limited to the density values. For example, the medical image data may be displayed in a partial display area using, as the display condition, an enlargement and reduction function, a display position parallel movement function, a graphic drawing function, a density value measurement function, or the like, on the entire image. FIG. 5 shows a display example in the case where the left lung-field region of the thumbnail 103 is selected. First, the medical image data corresponding to the thumbnail 103 is subjected to tone conversion using density values suitable for a lung-field region (e.g., WL: −600, WW: 1500) such that their tones are adjusted to those that can be displayed on the display unit 36. Furthermore, the display position of medical image data is moved in parallel such that the left lung-field region is displayed at the center position of the partial display area 108. Then, medical image data obtained by enlarging the entire image to have a size at which the left lung-field region can be easily observed is displayed in the partial display area 108. Furthermore, a histogram of the density values in the left lung-field region calculated using a known density value measurement function is displayed in the partial display area 110.

The display condition corresponding to the selected area is set in advance, for example, as shown in Table 2, according to the image information obtained from the DICOM header or the like and the selected thumbnail divided area. As shown in Table 2, a display condition is determined according to a modality used to capture the medical image data and an image capture site. The medical image data corresponding to the selected thumbnail is displayed in the main display area in a display condition corresponding to the image information of the medical image data and the selected partial area. The enlargement ratio "Fit" in Table 2 refers to an enlargement ratio that sets the size at which the corresponding area can be seen in the largest view, and "center" in the parallel movement in Table 2 refers to a condition for moving the entire image in parallel such that the corresponding area is displayed at the center of the partial display area. The table as shown in Table 2 is stored in, for example, the storage unit 34 or the like.

As described above, according to the first embodiment, designation of medical image data that is to be displayed in the main display area and designation of a display condition that is to be applied thereto can be simultaneously performed, and, thus, the effort required to display medical image data can be reduced. Furthermore, according to Modified Example 2, in addition to the designation of medical image data and the designation of a display condition, selection of a partial display area in which the medical image data is to be displayed can be performed with a simple operation, and, thus, the operability is further improved.

In the foregoing embodiment, an example was shown in which the main display area 102 is divided into four equal partial display areas, but the number of areas obtained by the division is not limited to four, and, for example, as shown in FIGS. 12A and 12B, the partial display areas may not have the same size. Furthermore, the main display area may not be divided. In this case, in the main display area 102, medical image data (one medical image) selected at the latest point in time is displayed in a display condition corresponding to a partial area specified when the thumbnail was selected. In the foregoing embodiment, the dividing lines 112 to 114 are used to clearly define the partial areas in the thumbnail, but these dividing lines may not be drawn

TABLE 2

| Image information | | | Display condition | | | |
|---|---|---|---|---|---|---|
| Modality | Image capture site | Region | Density value | Enlargement ratio | Parallel movement | Histogram |
| CT | Breast region | Lung-field | WL: −600 WW: 1500 | Fit | Center | Displayed |
| CT | Breast region | Bone | WL: 500 WW: 2500 | No change | Center | Not displayed |
| CT | Breast region | Others | WL: 60 WW: 400 | No change | No change | Not displayed |
| CT | Abdominal region | Liver | WL: 60 WW: 400 | Fit | Center | Displayed |
| CT | Abdominal region | Stomach | WL: 60 WW: 400 | Fit | No change | Displayed |
| CT | Abdominal region | Lung-field | WL: −600 WW: 1500 | Fit | Center | Displayed |
| CT | Abdominal region | Others | WL: 60 WW: 400 | No change | No change | Not displayed |
| Others | All | None | No change | No change | No change | Not displayed |

Modified Example 2

In this embodiment, in step S204, a partial display area in which the medical image data corresponding to the selected thumbnail is to be displayed is selected according to a predetermined rule, but there is no limitation to this. For example, a configuration is possible in which the user can designate a partial display area in which medical image data is to be displayed, by dragging and dropping the thumbnail onto a freely selected partial display area in the main display area. More specifically, the pointer 115 is moved onto a freely selected partial area in a freely selected thumbnail, dragging is started, and the pointer is moved onto a freely selected partial display area, after which the pointer is released (dropped). According to Modified Example 2, medical image data corresponding to a freely selected thumbnail can be displayed in a freely selected partial display area in a suitable display condition (a display condition suitable for an anatomical area corresponding to the partial area specified with a pointer when the dragging was started).

or overlaid. Note that, if the dividing lines 112 to 114 are displayed on the thumbnail, the user can more clearly recognize the divided areas in the thumbnail. Note that the image information and the display condition described above are merely examples, and the present invention is not limited to these examples.

Second Embodiment

In the first embodiment, partial areas corresponding to anatomical areas of medical image data are set in a thumbnail. The image display apparatus 10 according to the second embodiment further divides the thumbnail into a plurality of divided areas, according to a division condition of the main display area 102 into partial display areas. According to a partial area and a divided area specified when the thumbnail was selected, the image display apparatus 10 displays medical image data corresponding to the selected thumbnail, in a display condition corresponding to the selected partial area, in a partial display area associated with the selected divided area.

Figure 6:
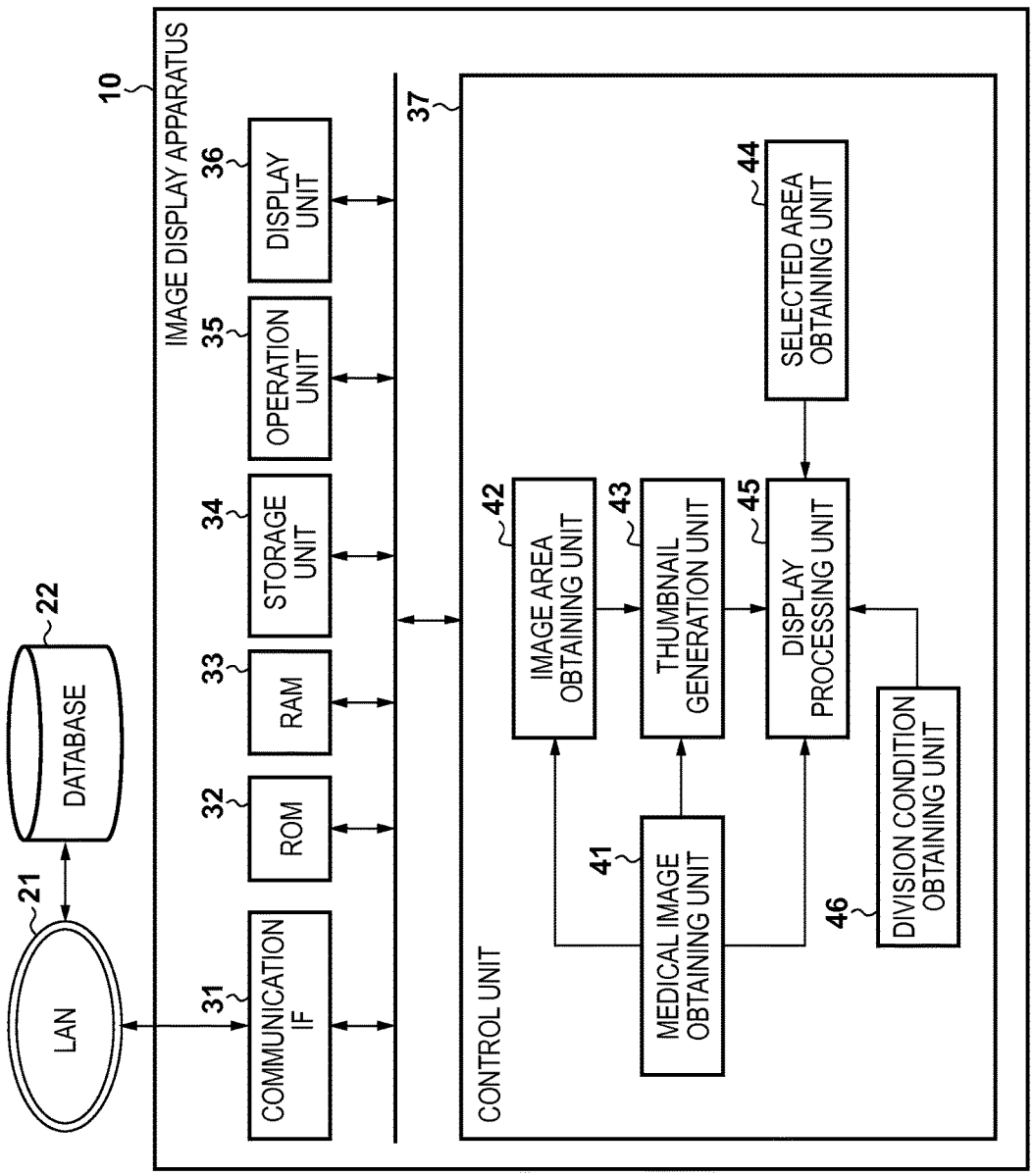
FIG. 6 is a block diagram of a medical image display system according to a second embodiment.

FIG. 6 shows a configuration example of the image display apparatus 10 according to the second embodiment. Comparison with the configuration example of the image display apparatus 10 according to the first embodiment (FIG. 1) shows that a division condition obtaining unit 46 has been added. The constituent elements other than the division condition obtaining unit 46 shown in the drawing are similar to those in FIG. 1. The division condition obtaining unit 46 obtains a division condition of the main display area displayed on the display unit 36 into a plurality of partial display areas, and outputs it to the display processing unit 45. It is assumed that, as in the first embodiment, each functional unit is realized by software.

Figure 7:
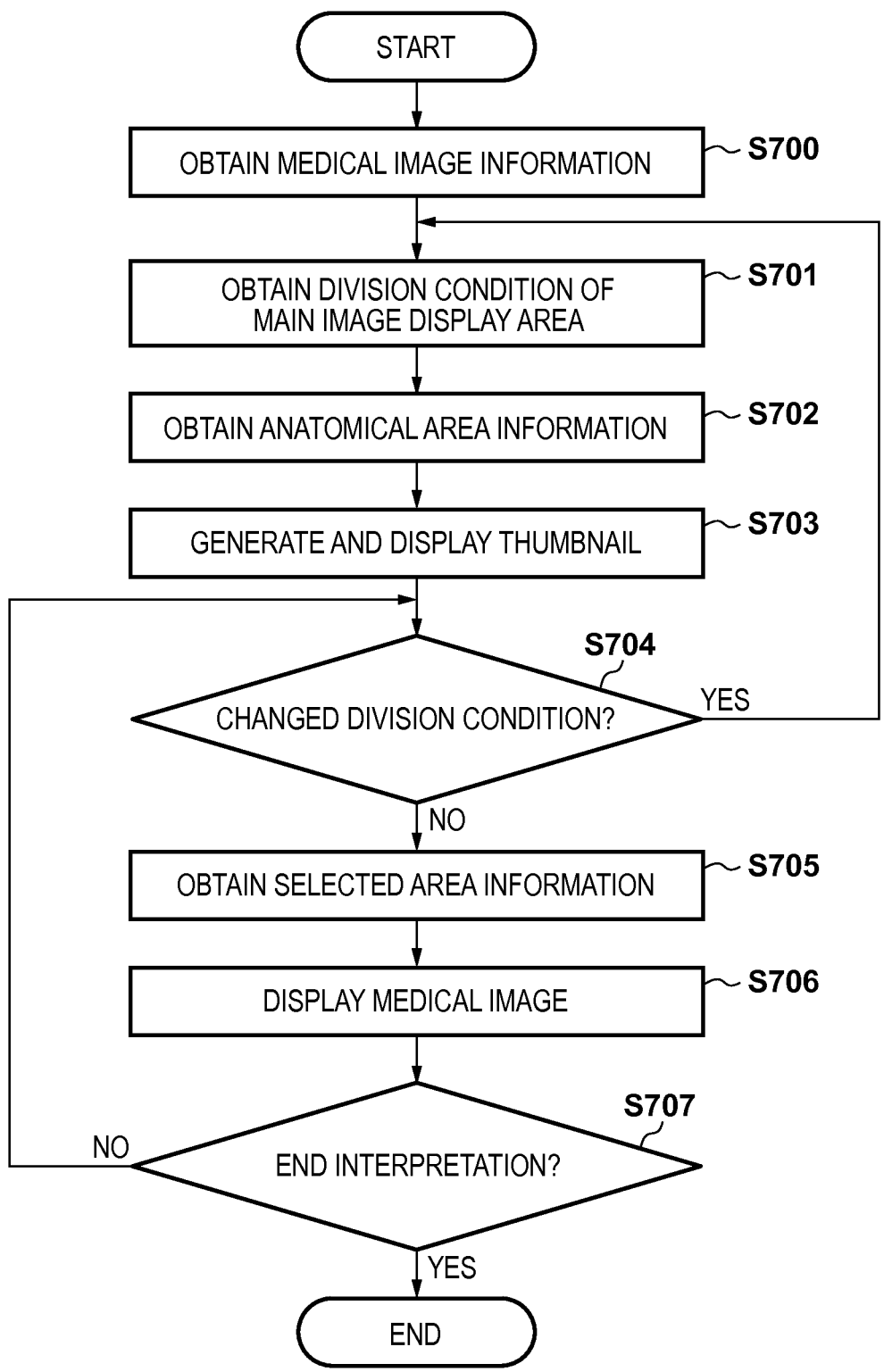
FIG. 7 is a flowchart illustrating the overall processing in the second embodiment.
Figure 8A:
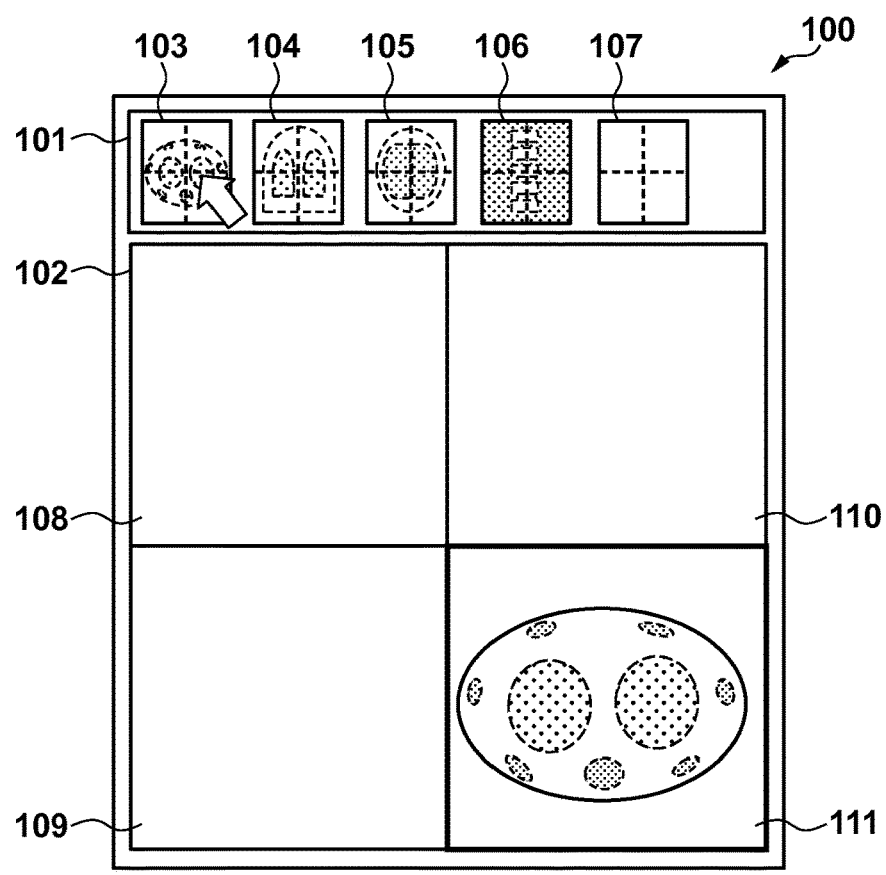
FIGS. 8A and 8B are diagrams showing a screen configuration example according to the second embodiment.
Figure 8B:
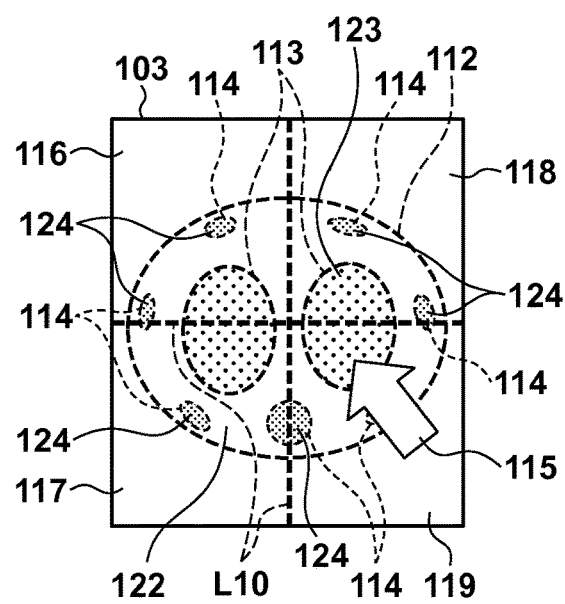

Next, the processing procedure by the control unit 37 in the second embodiment will be described with reference to FIGS. 7, 8A, and 8B. FIG. 7 is a flowchart illustrating the processing performed by the control unit 37. FIG. 8A is an exemplary screen displayed on the display unit 36 through processing (described later). FIG. 8B shows an enlarged view of an image of the thumbnail 103 shown in FIG. 8A.

The process in step S700 is similar to that in step S200 in the first embodiment. In step S701, the division condition obtaining unit 46 obtains a division condition of the main display area 102 displayed on the display unit 36. For example, if the number of areas obtained by the division in the main display area 102 is taken as l, the number of rows n is taken as n, and the number of columns is taken as m, (l, n, m)=(4, 2, 2) is obtained in the case of the division state of the main display area 102 as shown in FIG. 8A. Note that the method for obtaining the division condition described above is merely an example, and the present invention is not limited to this example.

The process in step S702 is similar to that in step S201 in the first embodiment. In the process in step S703, the following process is performed in addition to the process in step S202 in the first embodiment. The thumbnail generation unit 43 divides the thumbnail according to the division condition obtained in step S701. For example, if (l, n, m)=(4, 2, 2) is obtained in step S701, the thumbnail generation unit 43 divides the thumbnail as well in a similar manner according to the condition (l, n, m)=(4, 2, 2). That is to say, the reduced image forming the thumbnail is divided according to an arrangement of the plurality of partial display areas in the main display area 102, into a plurality of divided areas, and the plurality of divided areas and the plurality of partial display areas in the main display area 102 are respectively associated with each other. For example, if the main display area 102 is divided as shown in FIG. 8A, divided areas 116 to 119 are obtained as shown in FIG. 8B, and are respectively associated with the partial display areas 108 to 111. Subsequently, dividing lines (L10 in FIG. 8B) are generated such that the divided areas can be seen, and a thumbnail is generated in which the dividing lines are drawn or overlaid on the reduced image.

In the thumbnail 103 in FIG. 8B, partial areas are extracted according to the anatomical areas obtained in step S702 from the reduced image forming the thumbnail, and, thus, the partial areas 122 to 124 are obtained. Furthermore, the reduced image forming the thumbnail 103 is divided according to the division condition of the main display area 102, and, thus, the divided areas 116 to 119 are obtained. In this manner, as shown in FIG. 8B, a thumbnail 103 is generated in which the dividing lines 112 to 114 and the dividing lines L10 are drawn or overlaid on the reduced image.

In step S704, the control unit 37 obtains a division condition of the main display area, and judges whether or not the division condition has been changed. Note that the division condition of the main display area 102 can be changed in response to an instruction from the user received via the operation unit 35. A method for changing the number of areas obtained by the division can be realized by a known technique used by a conventional medical image viewer, and, thus, a description thereof has been omitted. In step S704, if it is judged that the division condition has not been changed, the procedure advances to step S705, and, if it is judged that the division condition has been changed, the procedure returns to step S701.

The process in step S705 is similar to that in step S203 in the first embodiment. However, the obtained selected area information is two types of area information described below. That is to say, the area information refers to:
  first area information of areas that have been divided according to anatomical area information (i.e., one of the partial areas 122 to 124 in the example in FIGS. 8A and 8B); and
  second area information of areas that have been divided according to a division condition of the main display area (i.e., one of the divided areas 116 to 119 in the example in FIGS. 8A and 8B).

In step S706, the display processing unit 45 displays the medical image data corresponding to the thumbnail selected in step S705, in a display condition corresponding to the first area information selected in step S705, in a partial display area corresponding to the second area information. In the example in FIG. 8B, the pointer 115 designates a portion belonging to the divided area 119, in the partial area 123 that is a lung-field region. Accordingly, the partial area 123 (lung-field region) in the thumbnail 103 is selected as the first area information, and the divided area 119 (the lower right area) is obtained as the second area information. As a result, as shown in FIG. 8A, the medical image data corresponding to the thumbnail 103 is displayed in the partial display area 111, in a display condition suited to observe a lung-field region (e.g., WL: −600, WW: 1500). If another piece of image data has been already displayed in the partial display area 111, the display processing unit 45 deletes the already displayed image data from the partial display area 111, and, then, displays the medical image data corresponding to the thumbnail 103. Note that, when deleting a medical image that is being displayed, the user may be asked whether or not that image may be deleted.

The process in step S707 is similar to that in step S205 in the first embodiment, and it is judged whether or not an instruction to end the interpretation has been received. If an instruction to end the interpretation has been received, the procedure in FIG. 7 is ended, and, if an instruction to end the interpretation has not been received, the procedure returns to step S704.

As described above, with the image display apparatus according to the second embodiment, the following effects are obtained. That is to say, if any partial area and any divided area in any selected thumbnail are selected, medical image data corresponding to the thumbnail can be displayed in a display condition corresponding to the selected partial area, and in a partial display area associated with the selected divided area. Accordingly, with a single selecting operation, freely selected medical image data can be displayed in a freely selected partial display area in a display condition suited to perform interpretation, and, thus, the user effort can be reduced.

Note that the dividing lines (e.g., L10 in FIG. 8B) indicating the division of the main display area may be omitted. The reason for this is that, for example, if the division state of the main display area 102 is not so much complicated as shown in FIG. 8A, the user can see correspondence between the four partial display areas 108 to 111 and the positions on the reduced image forming the thumbnail even when the dividing lines L10 are omitted.

Third Embodiment

With the image display apparatus 10 according to the third embodiment, when selecting the thumbnail, the user can select any partial area in the reduced image forming the thumbnail, and can give directional information specifying a partial display area. The image display apparatus 10 displays the medical image data corresponding to the selected thumbnail, in a partial display area specified by the directional information among the plurality of partial display areas in the main display area, in a display condition suitable for an anatomical area corresponding to the selected partial area.

Figure 9:
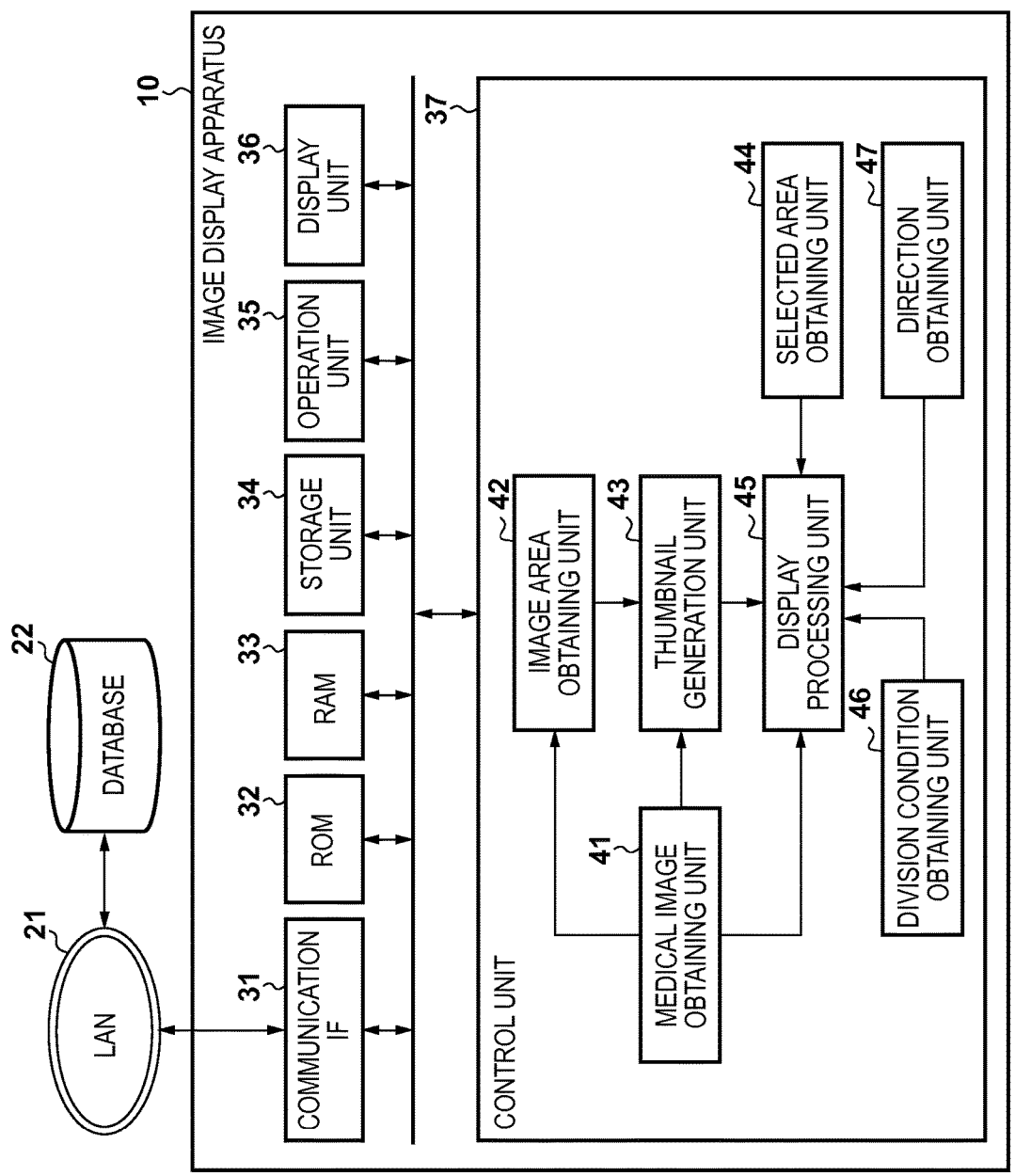
FIG. 9 is a block diagram of a medical image display system according to a third embodiment.

FIG. 9 shows a configuration example of an image display apparatus according to this embodiment. Comparison with the configuration example according to the second embodiment (FIG. 6) shows that a direction obtaining unit 47 has been added. The constituent elements other than the direction obtaining unit 47 are similar to those in FIG. 6. The direction obtaining unit 47 obtains directional information input by the user via the operation unit 35 on a thumbnail displayed on the display unit 36, and outputs it to the display processing unit 45. For example, the direction obtaining unit 47 obtains directional information, based on a direction in which the thumbnail is dragged or flicked. Furthermore, as described later, the division condition obtaining unit 46 obtains center positions of the respective partial display areas in the main display area. It is assumed that, as in the second embodiment, each functional unit is realized by software.

Figure 10:
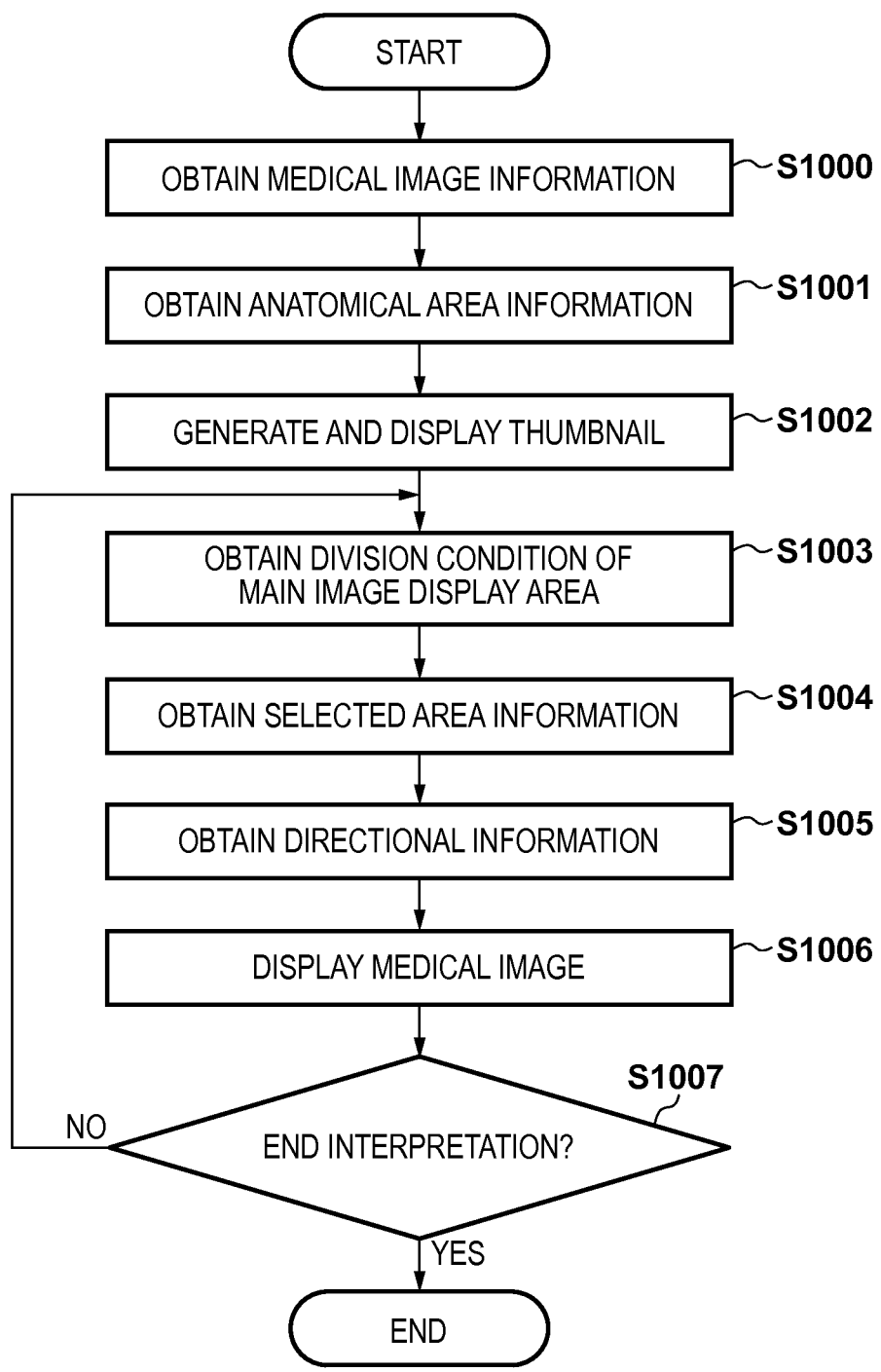
FIG. 10 is a flowchart illustrating the overall processing of the third embodiment.
Figure 11:
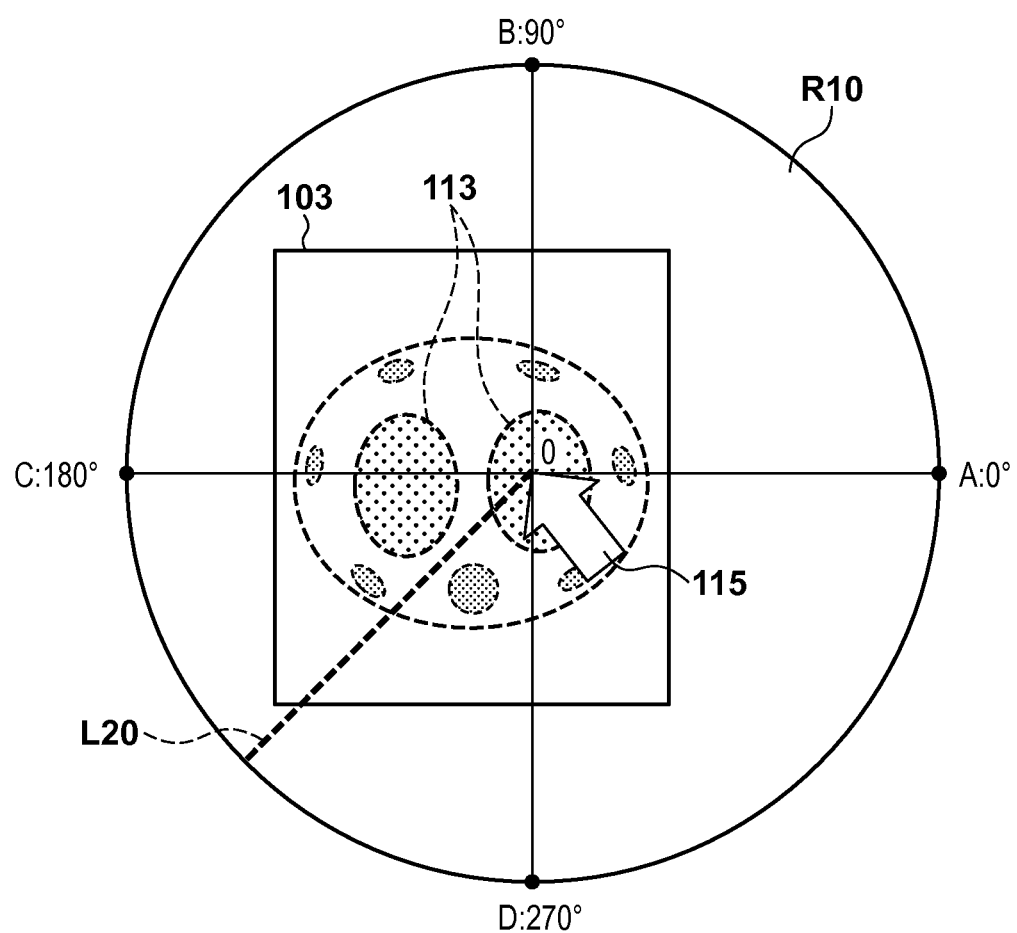
FIG. 11 is a diagram illustrating a method for inputting directional information on a thumbnail.

Next, the overall processing by the control unit 37 in the third embodiment will be described with reference to FIGS. 10 and 11. FIG. 10 is a flowchart of the processing performed by the control unit 37. FIG. 11 is a diagram illustrating a method in which the user inputs directional information on the thumbnail 103 shown in FIG. 3B. The pointer 115 is, for example, a mouse pointer, and indicates positional information controlled by the operation unit 35. R10 denotes a circle in which the position indicated by the pointer 115 is taken as a center O. When the right direction of the pointer 115 is taken as 0°, points at which straight lines extending from the center O in directions of 0°, 90°, 180°, and 270° intersect the circle R10 can be respectively taken as A, B, C, and D.

The processes in steps S1000 to S1002 are similar to those in steps S200 to S202 in the first embodiment. The process in step S1003 is similar to that in step S701 in the second embodiment. The process in step S1004 is similar to that in step S203 in the first embodiment.

In step S1005, the user inputs directional information on the thumbnail divided area selected in step S1004, via the operation unit 35. For example, the directional information is input using a pointing device that is not shown to drag the partial area 123 in the thumbnail 103 shown in FIG. 3B in a freely selected direction. Alternatively, if the display unit 36 is a touchscreen monitor, the directional information may be input on the partial area 123 in the thumbnail 103, using an operation method commonly referred to as flick. For example, in FIG. 11, if the thumbnail 103 is tapped (flicked) with a finger in the direction A, the directional information 0° is input. Furthermore, for example, if the thumbnail is tapped (flicked) with a finger in a direction along the line segment L20 shown exactly at the middle between the line segment OC and the line segment OD, the directional information 225° is input.

In step S1006, the display processing unit 45 selects one of the plurality of partial display areas in the main display area, according to the division condition of the main display area obtained in step S1003 and the directional information obtained in step S1005. The display processing unit 45 displays the medical image data corresponding to the selected thumbnail, in the selected partial display area. At that time, the medical image data is displayed in a display condition corresponding to the partial area selected in step S1004. The selected partial area is, for example, a partial area in the thumbnail specified by a position at which the dragging or the flicking was started. The display condition is determined according to the methods shown in step S204 in the first embodiment or Modified Example 1 of the first embodiment.

Hereinafter, a case will be described in which the directional information input in step S1005 on the partial area 123 in the thumbnail 103 shown in FIG. 3B is within a range of 0° to 90° shown in FIG. 11. In this case, the directional information is taken as the upper right direction, and the medical image data corresponding to the thumbnail 103 is displayed in the partial display area 110 arranged in the upper right in the main display area 102 in FIG. 3A, in a display condition corresponding to the partial area 123. If the input directional information is within a range of 90° to 180°, the medical image data is displayed in the partial display area 108 in the main display area 102, in a display condition corresponding to the partial area 123. If the input directional information is within a range of 180° to 270°, the medical image data is displayed in the partial display area 109 in the main display area 102, in a display condition corresponding to the partial area 123 (lung-field region). If the input directional information is within a range of 270° to 0°, the medical image data is displayed in the partial display area 111 in the main display area 102, in a display condition corresponding to the partial area 123.

Hereinafter, a relationship between the range of input directional information and the partial display area selected according to that range will be described in more detail with reference to FIGS. 12A and 12B. In FIG. 12A, the main display area 102 is divided into four partial display areas (the partial display areas 108 to 111). Note that the partial display areas 108 to 111 do not have the same size, and their arrangement is different from that in FIG. 3A. In the drawing, Oa denotes the center of the main display area 102, Ob denotes the center of the partial display area 108, Oc denotes the center of the partial display area 109, Od denotes the center of the partial display area 110, and Oe denotes the center of the partial display area 111. In FIG. 12B, a circle centered about Oa is denoted by R20. The line segment dividing the angle formed by Ob→Oa→Oe into two equal angles is denoted by L21, the line segment dividing the angle formed by Ob→Oa→Oc into two equal angles is denoted by L22, the line segment dividing the angle formed by Oc→Oa→Od into two equal angles is denoted by L23, and the line segment dividing the angle formed by Od→Oa→Oe into two equal angles is denoted by L24. The intersection between line segment L21 and R20 is denoted by E, the intersection between line segment L22 and R20 is denoted by F, the intersection between line segment L23 and R20 is denoted by G, and the intersection between line segment L24 and R20 is denoted by H. If the directional information input is within the range of the angle formed by E→Oa→F, the partial display area 108 having the center Ob in that range is selected. In a similar manner, if the directional information input is within the range of the angle formed by F→Oa→G, the partial display area 109 is selected. In a similar manner, if the directional information input is within the range of the angle formed by G→Oa→H, the partial display area 110 is selected. In a similar manner, if the directional information input is within the range of the angle formed by H→Oa→E, the partial display area 111 is selected.

In this manner, if the range of directional information is determined according to an angle formed by the centers of the partial display areas and the center of the main display area, a partial display area corresponding to the range of directional information can be determined. Note that, if the division condition of the main display area is, for example, (l, n, m)=(9, 3, 3), the center partial display area cannot be selected according to the above-described method. In this case, selection may be performed by performing an operation different from the operation that inputs the directional information on the thumbnail. The different operation is an operation such as pinch-in, pinch-out, or double-tapping on a touchscreen. Note that these operations are merely examples, and other operations may be performed.

The process in step S1007 is similar to that in step S205 in the first embodiment, and it is judged whether or not an instruction to end the interpretation has been received. If an instruction to end the interpretation has been received, the procedure in FIG. 10 is ended, and, if an instruction to end the interpretation has not been received, the procedure returns to step S1003.

As described above, with the image display apparatus according to the third embodiment, the following effects are obtained. That is to say, if directional information is given to a freely selected partial area in a freely selected thumbnail, medical image data corresponding to the thumbnail can be displayed in a partial display area determined according to the input directional information, in a display condition corresponding to the partial area to which the directional information was given. Accordingly, it is possible to provide an image display apparatus and an image display method that that require less effort to display an image in a partial display area intended by the user, in a display condition intended by the user.

As described above, according to the foregoing embodiments, partial areas corresponding to anatomical areas are set in a reduced image displayed in the thumbnail, and display conditions according to the anatomical areas are associated with the partial areas. The user can specify any partial area from among the set partial areas with an operation that selects the thumbnail, and, thus, the user can designate medical image data that is to be displayed and a display condition that is to be applied, with the operation that selects the thumbnail. Thus, the foregoing embodiments are effective in that data corresponding to the selected thumbnail can be displayed in the main display area in a freely selected display condition, with a simple user operation.

In the foregoing embodiments, the thumbnail display area and the main display area are displayed in the same display screen, but the thumbnail display area and the main display area may be displayed on different display units. Furthermore, when obtaining a display condition corresponding to a partial area in the thumbnail, association between partial areas and anatomical areas as shown in FIG. 3C is managed, and a display condition corresponding to a partial area is obtained based on an anatomical area, but there is no limitation to this. For example, management may be performed such that display conditions are directly associated with respective partial areas, and a display condition of a specified partial area may be obtained. In this case, the field of the anatomical areas in FIG. 3C indicates the display conditions.

As described above, according to the first to third embodiments, it is possible to display freely selected medical image data, in a display condition suitable for an area that is to be observed, with a simple operation.

Fourth Embodiment

In the first to third embodiments described above, in response to selection of a thumbnail, medical image specified by the selected thumbnail is displayed in the main display area 102 in different display conditions according to a designated position with the pointer 115 in the selected thumbnail. In the fourth embodiment, a configuration will be described in which medical images generated with different display conditions are stored in the database 22, and a medical image generated in a display condition according to a designated position with the pointer 115 in a thumbnail is selected from among the stored medical images, and is displayed in the main display area 102.

Typically, captured image data obtained by a medical image capturing apparatus is subjected to various types of image processing. In the case where different medical images generated by performing different image processing on the same captured image data are stored as different medical images in a data server in a hospital, if the number of types of image processing performed on the same captured image data increases, the number of medical images stored also increases.

As a technique for managing such a large number of medical images, Japanese Patent Laid-Open No. 2012-81180 (Document 2) discloses a technique for classifying and displaying thumbnails corresponding to medical images. Accordingly, it is possible to search for and display a medical image targeted by a user, by searching for a target thumbnail.

However, as the amount of medical images increases, the number of thumbnails also significantly increases, and a longer time is required to perform a search. Furthermore, a longer time is required for a user to find an intended thumbnail. Thus, in the fourth embodiment, a configuration will be described in which, even when the number of medical images increases, medical images intended by a user can be displayed without complicated operations by the user.

Figure 13:
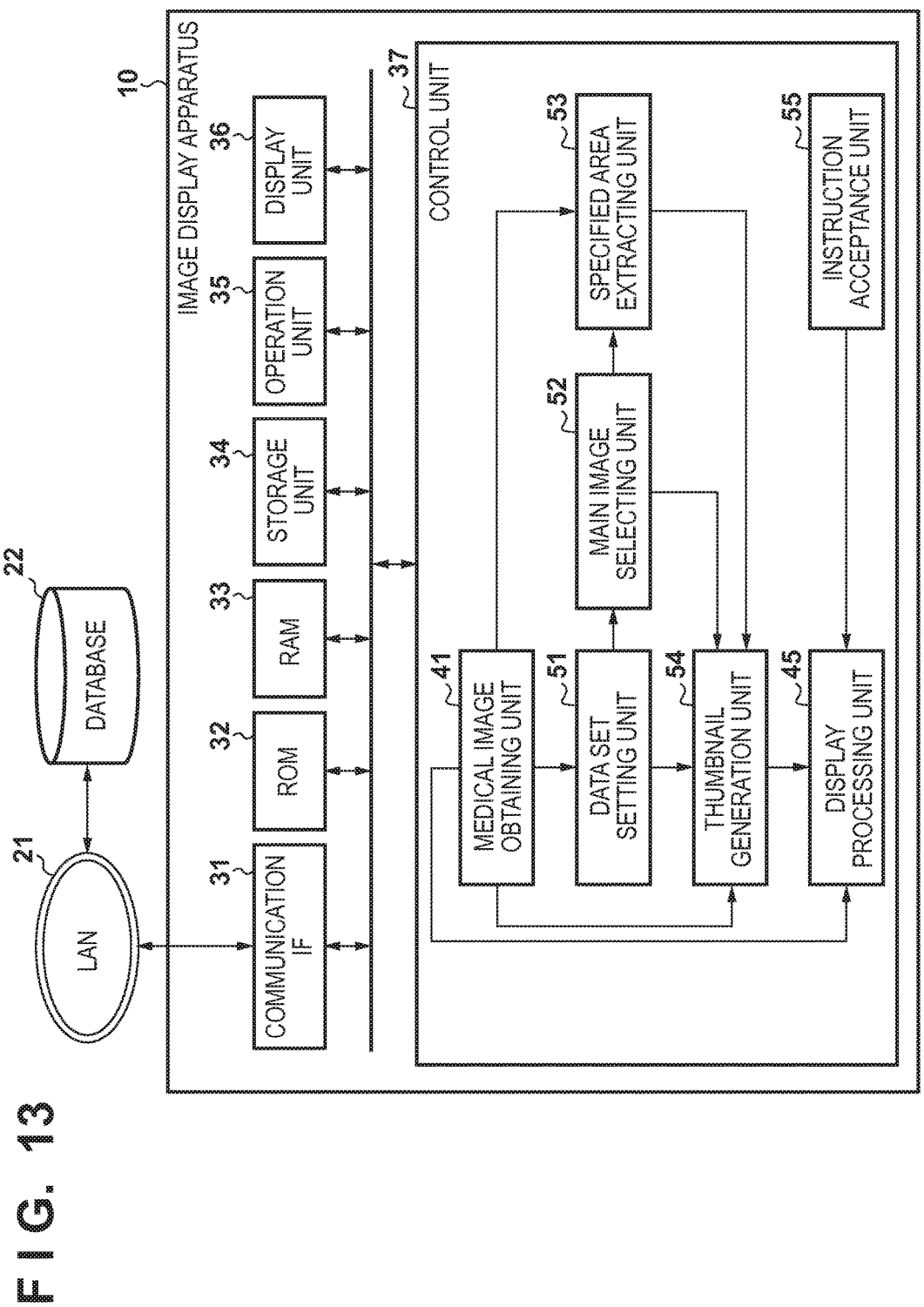
FIG. 13 is a diagram showing a medical image display system.

FIG. 13 is a diagram showing a medical image display system according to the fourth embodiment. In the drawing, the same constituent elements as those in the first embodiment (FIG. 1) are denoted by the same reference numerals. The control unit 37 has a functional configuration including the medical image obtaining unit 41, a data set setting unit 51, a main image selecting unit 52, a specified area extracting unit 53, a thumbnail generation unit 54, an instruction acceptance unit 55, and the display processing unit 45. These functions are realized by the CPU reading and executing programs stored in the ROM 32 or the like.

The medical image obtaining unit 41 obtains part or all of medical images of a patient via the communication IF 31 and the LAN 21 from the database 22, according to a user operation input by the operation unit 35. The medical image is, for example, image data such as CT image data. The medical image obtaining unit 41 outputs the obtained medical image to the data set setting unit 51, the specified area extracting unit 53, the thumbnail generation unit 54 and the display processing unit 45.

The data set setting unit 51 selects a medical image group from which a common thumbnail is to be generated, according to a rule (described later), from among the medical images obtained from the medical image obtaining unit 41, and sets the group as a data set. The data set setting unit 51 outputs the set data set to the main image selecting unit 52 and the thumbnail generation unit 54. If a plurality of data sets are set, the data set setting unit 51 gives identification information to each data set. The data set setting unit 51 outputs each data set and the identification information in association with each other.

The main image selecting unit 52 selects a medical image mainly used to generate a thumbnail (hereinafter, referred to as a main image), from among the medical images included in the data set that is set by the data set setting unit 51, according to a rule (described later). The main image selecting unit 52 outputs the selected main image to the specified area extracting unit 53 and the thumbnail generation unit 54. If a plurality of data sets are set by the data set setting unit 51, the main image selecting unit 52 selects a main image for each data set. The main image selecting unit 52 outputs the main image and the identification information of each data set in association with each other.

The specified area extracting unit 53 obtains the main image selected by the main image selecting unit 52, from the medical image obtaining unit 41 and performs image processing (described later) on the main image. Furthermore, the specified area extracting unit 53 extracts specified areas in the main image, according to a rule (described later). A specified area is part of the area of a medical image, and is an example of a partial area. The specified area extracting unit 53 outputs specified area information indicating the specified areas to the thumbnail generation unit 54. If a plurality of data sets are set by the data set setting unit 51, specified areas are set for a main image of each data set, and specified area information of each specified area is output.

The thumbnail generation unit 54 generates a thumbnail based on the medical images included in the data set, the main image selected by the main image selecting unit 52, and the specified areas set by the specified area extracting unit 53. The thumbnail is an example of a reduced image. At that time, the thumbnail generation unit 54 generates a common thumbnail for each data set that is set by the data set setting unit 51. The thumbnail generation unit 54 outputs the thumbnail to the display processing unit 45.

The instruction acceptance unit 55 accepts various instructions input by the user via the operation unit 35. For example, when a specified area included in the thumbnail displayed on the display unit 36 is selected by the user using the operation unit 35, the instruction acceptance unit 55 outputs the selection instruction to the display processing unit 45.

The display processing unit 45 displays various types of information on the display unit 36. The display processing unit 45 displays, for example, the thumbnail generated by the thumbnail generation unit 54. The display processing unit 45 obtains a medical image corresponding to the selection instruction obtained by the instruction acceptance unit 55, from the medical image obtaining unit 41, and displays the medical image.

Note that at least part of the units included in the control unit 37 may be realized by an independent apparatus. Furthermore, each unit may be realized by software for realizing the function. In this case, software for realizing the function may operate on a server via a network such as cloud. In this embodiment, it is assumed that each constituent element is realized by software in a local environment.

Figure 14:
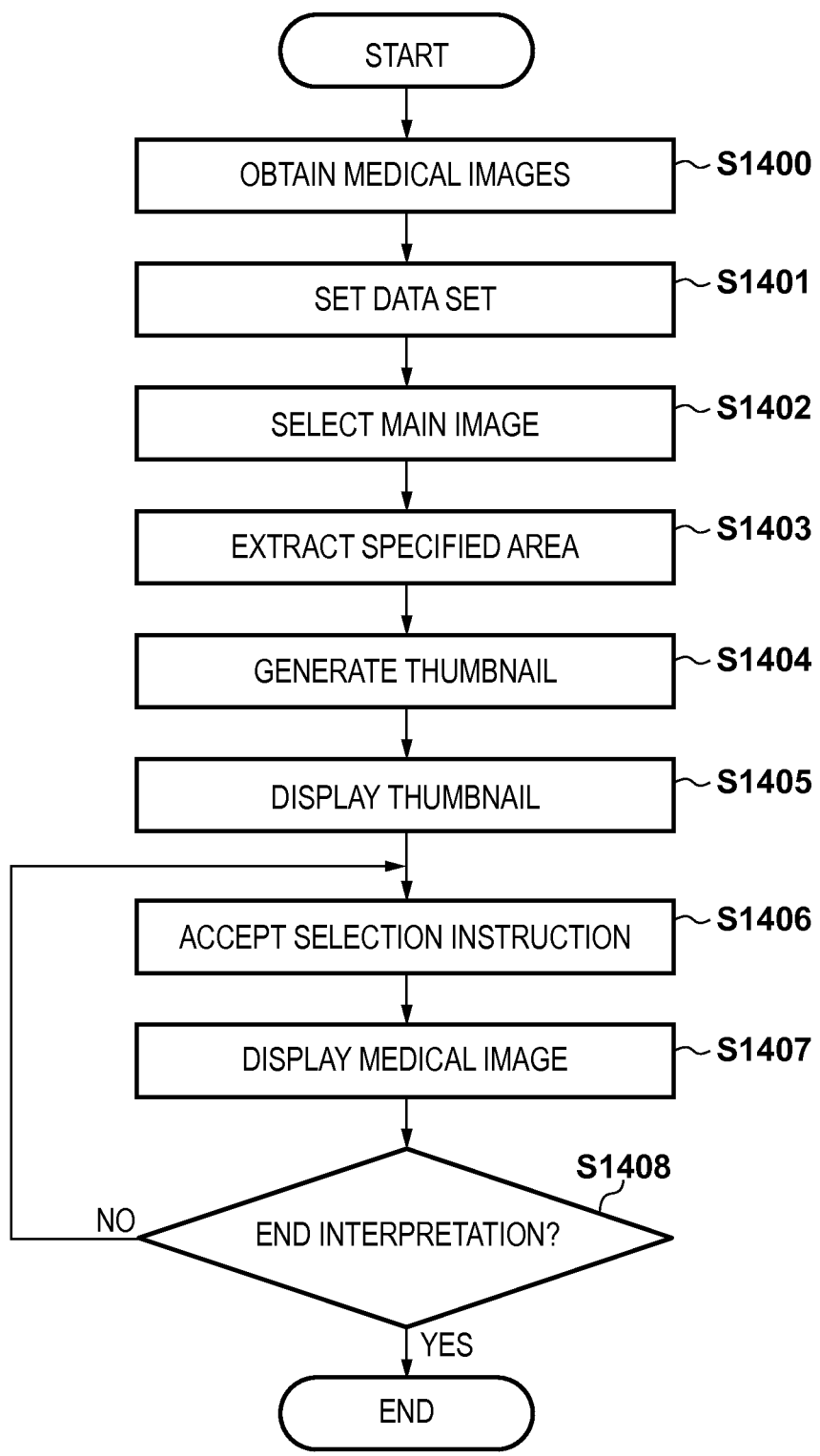
FIG. 14 is a flowchart illustrating medical image display processing.

FIG. 14 is a flowchart illustrating image display processing performed by the image display apparatus 10. Hereinafter, a medical image generated when an image of a breast region is captured by an X-ray CT apparatus will be described as an example, but the type of medical image is not limited to those in this embodiment. In step S1400, the medical image obtaining unit 41 reads medical images via the communication IF 31 and the LAN 21 from the database 22, according to a user operation input by the operation unit 35.

Next, in step S1401, the data set setting unit 51 sets a data set (data set setting processing). Specifically, the data set setting unit 51 selects medical images from which a common thumbnail is to be generated, from among the medical images read in step S1400, according to a data set setting condition. The data set setting unit 51 sets the selected medical images as a data set. The data set setting condition is based on information included in medical images, and is, for example, set in advance in the storage unit 34 or the like.

Examples of the setting condition include "image capture dates are within a certain period of time", "image capturing modalities are the same", "projection data is the same", and the like. Note that the data set setting condition is not limited to those in the embodiment. Furthermore, the setting condition may be designated by the user. The data set setting unit 51 obtains such included information from header information of DICOM, which is the standard for medical images.

For example, it is assumed that the data set setting condition "projection data is the same" is set. In this case, the data set setting unit 51 searches for and obtains medical images generated by performing different types of image processing on the same projection data, based on the DICOM header, from among the medical images read in step S1400. The obtained medical images are set as a data set.

Hereinafter, different medical images generated from the same projection data will be described. Typically, a CT image generated by an X-ray CT apparatus is obtained through convolution of projection data obtained by capturing an image of a subject and a predetermined reconstruction function. Reconstruction functions can be designed as appropriate, and an appropriate reconstruction function is used according to a clinical purpose.

Accordingly, a plurality of CT images may be generated using a plurality of reconstruction functions on the same projection data. For example, in the case of a CT image of a breast region, typically, a lung-field window setting image and a mediastinal window setting image may be generated. Furthermore, a bone window setting image may be generated. A lung-field window setting image is a medical image generated using a reconstruction function suited to observe a lung-field region. A mediastinal window setting image is a medical image generated using a reconstruction function suited to observe a mediastinal region. In a similar manner, a bone window setting image is a medical image generated using a reconstruction function suited to observe a bone.

It is assumed that a lung-field window setting image and a mediastinal window setting image are generated from the same projection data, and are stored in the database 22. In this case, a lung-field window setting image and a mediastinal window setting image obtained from the same projection data are selected, and are set as a data set corresponding to a common thumbnail.

Returning to the flowchart in FIG. 14, in step S1402, the main image selecting unit 52 selects a main image, from among the medical images included in the data set that is set by the data set setting unit 51, according to a main image selecting condition (main image selection processing). The main image selecting condition is based on information included in medical images, and is, for example, set in advance in the storage unit 34 or the like. Examples of the main image selecting condition include "medical image generated at the earliest point in time", "medical image having the largest window width", "medical image having the largest data amount", and the like. Note that the main image selecting condition is not limited to those in the embodiment.

For example, it is assumed that the selecting condition "medical image having the largest window width" is set. In this case, the main image selecting unit 52 obtains window widths from the DICOM header information of the medical images included in the data set, and selects a medical image having the largest window width as a main image.

Furthermore, it is assumed that the medical images included in the data set are a lung-field window setting image and a mediastinal window setting image. Typically, a lung-field window setting image has a window width of approximately 1500, and a mediastinal window setting image has a window width of approximately 400. Accordingly, in this case, a lung-field window setting image is set as a main image. Note that the main image selecting condition is not limited to those in the embodiment.

Next, in step S1403, the specified area extracting unit 53 extracts specified areas (partial areas) from the main image selected in step S1402, according to a specified area extracting condition (partial area extraction processing). The specified area extracting condition is based on information included in medical images, and is, for example, set in advance in the storage unit 34 or the like. The extracting condition according to this embodiment is a condition for extracting predetermined anatomical areas. After extracting the specified areas, the specified area extracting unit 53 refers to the included information, and stores the specified areas and the medical images showing the specified areas in association with each other in the storage unit 34 or the like.

Hereinafter, the extracting condition will be described. For example, it is assumed that the medical images included in the data set are a lung-field window setting image and a mediastinal window setting image that are CT images of a breast region. For such a data set, for example, the extracting condition is determined in which, if the main image is the lung-field window setting image, a lung-field region corresponding to the lung-field window setting image and a soft region corresponding to the mediastinal window setting image are extracted from the main image.

According to this extracting condition, the specified area extracting unit 53 first performs noise removal using a smoothing filter on the main image. Next, the specified area extracting unit 53 performs binarization processing using a predetermined threshold (e.g., HU value: −200) with respect to an image pixel value, thereby separating a region inside the body and a region outside the body from each other. The specified area extracting unit 53 further separates the region inside the body into a lung-field region and a soft region, using another threshold (e.g., HU value: −500), and extracts data of each area.

According to another example, it is assumed that the medical images included in the data set are a lung-field window setting image, a mediastinal window setting image, and a bone window setting image, and the main image is the lung-field window setting image. For such a data set, for example, the extracting condition is determined in which a lung-field region corresponding to the lung-field window setting image, a soft region corresponding to the mediastinal window setting image, and a bone region corresponding to the bone window setting image are extracted as specified areas.

According to this extracting condition, the specified area extracting unit 53 performs noise removal and obtains a region inside the body from the main image, and, then, further separates the region inside the body into a bone region and the other region, using another threshold (e.g., HU value: 300), and extracts data of each area. The specified area extracting unit 53 further separates the other region into a lung-field region and a soft region, using another threshold (e.g., HU value: −500), and extracts data of each area.

Note that the processing performed by the specified area extracting unit 53 is not limited to those in this embodiment. According to another example, the specified area extracting unit 53 may extract anatomically determined specified areas, using known organ segmentation processing such as graph cut processing.

In the image display apparatus 10, a specified area table is stored in the storage unit 34 or the like, and the specified area extracting unit 53 refers to the specified area table, and extracts a specified area from the main image based on the information included in the medical images included in the data set. Table 3 shows an example of a specified area table. As shown in the table, the specified area table stores included information and a specified area in association with each other. According to another example, the specified area extracting unit 53 may extract predetermined areas as specified areas from the main image regardless of the included information, and, then, may associate each medical image included in the data set with each area.

TABLE 3

| Included information | | Specified area |
|---|---|---|
| Modality | Image type | |
| CT | Lung-field window setting image | Lung-field |
| CT | Mediastinal window setting image | Soft region |
| CT | Bone window setting image | Bone |
| MRI | T1 image | White matter, grey matter |
| MRI | T2 image | Lateral ventricle |
| Bone scintigraphy | All | Bone |
| Myocardial perfusion scintigraphy | All | Heart |
| Bone mineral density | All | Bone |

Next, in step S1404, the thumbnail generation unit 54 generates a thumbnail (generation processing). That is to say, first, the thumbnail generation unit 54 selects a representative image corresponding to the main image selected in step S1402. For example, if the main image is a two-dimensional medical image (one slice image), the thumbnail generation unit 54 sets that main image, or an image obtained by extracting part of the main image, as a representative image.

On the other hand, if the main image is a three-dimensional medical image (a plurality of slice images), the thumbnail generation unit 54 selects a slice image representative of the main image as a representative image. Note that the slice image selected as a representative image is not limited to a slice image representative of the main image. According to another example, the representative image may be a slice image at a predetermined position (e.g., first slice image). According to another example, the representative image may be a slice image containing all specified areas corresponding to all medical images included in the data set to which the main image belongs, or may be a slice image containing the largest number of types of specified areas. Alternatively, the representative image may be an image obtained by extracting part of the slice image.

Next, the thumbnail generation unit 54 divides the representative image into areas, according to the specified areas extracted in step S1403. For example, it is assumed that lung-field regions, a soft region, and bone regions are extracted as specified areas in step S1403. In this case, the thumbnail generation unit 54 generates a thumbnail in which dividing lines are overlaid at the boundary positions between the specified areas contained in the representative image.

The thumbnail generated by the thumbnail generation unit 54 is, for example, as shown in FIG. 3B. The thumbnail 103 shown in FIG. 3B includes the partial areas 122 to 124 (hereinafter, referred to as lung-field regions 123, a soft region 122, and bone regions 124). Furthermore, as in the first embodiment, the thumbnail generation unit 54 draws the dividing lines 113 at the boundary positions between the lung-field regions 123 and the soft region 122, and draws the dividing lines 114 at the boundary positions between the soft region 122 and the bone regions 124. In this manner, the thumbnail is an image in which specified areas are identifiable. The dividing line 112 denotes the boundary position between the region outside the body and the region inside the body.

In FIG. 3B, the dividing lines 112, 113, and 114 are shown as broken lines, but the line type and the color of the dividing lines 112, 113, and 114 are not limited to those in the embodiment. That is to say, the dividing lines may be displayed as any lines, as long as a user can see boundary positions.

If a plurality of data sets are set in step S1401, the thumbnail generation unit 54 generates a thumbnail for each of the plurality of data sets.

Next, in step S1405, the display processing unit 45 displays the thumbnail on the display unit 36 (display processing). In step S1406, the instruction acceptance unit 55 accepts a selection instruction on a specified area (acceptance processing). Next, in step S1407, the display processing unit 45 specifies a medical image stored in association with the specified area according to the selection instruction, and displays the specified medical image on the display unit 36 (display processing).

Figure 15:
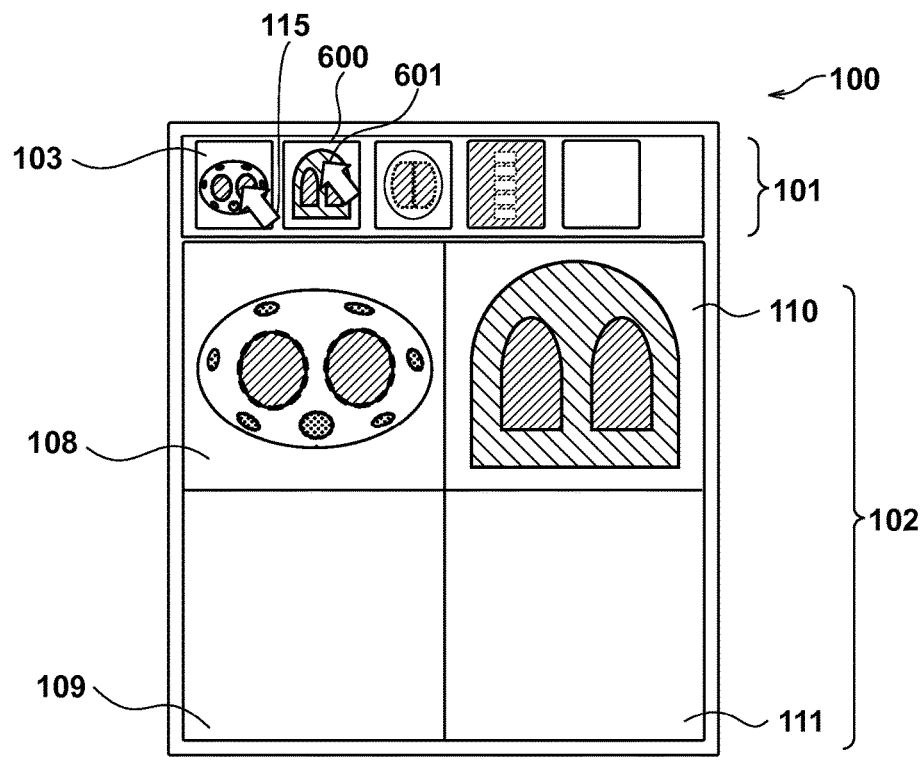
FIG. 15 is an explanatory diagram of the processes in steps S1406 and S1407.

FIG. 15 is a diagram illustrating the processes in steps S1406 and S1407. As shown in FIG. 15, the user operates the operation unit 35 while viewing the current input position with the pointer 115, thereby selecting a specified area in the thumbnail. The user selects a specified area, for example, in a thumbnail corresponding to medical image on which interpretation is to be performed or to which reference is to be made. The instruction acceptance unit 55 accepts input of the selection instruction indicating the specified area selected by the user. If the area selected by the user is an area corresponding to no medical image, such as a region outside the body, the instruction acceptance unit 55 does not accept the selection instruction.

For example, it is assumed that, as shown in FIG. 15, the lung-field region 123 (see FIG. 16A) in the thumbnail 103 is selected with a user operation. In this case, the display processing unit 45 displays the medical image corresponding to the lung-field region 123, in the main display area 102. Subsequently, as shown in FIG. 15, when a soft region 601 of a thumbnail 600 is selected with a user operation, the display processing unit 45 displays the medical image corresponding to the soft region 601, in the main display area 102.

As described above, when a medical image is displayed in the main display area 102, the user can give instructions to execute various functions on the displayed medical image. The image display apparatus 10 can execute various functions according to instructions accepted from the user. Examples of the functions include enlargement and reduction, density value conversion, display position parallel movement, graphic drawing, density value measurement, and the like, on the entire medical image.

In this embodiment, it is assumed that the display processing unit 45 displays corresponding medical images, in the same order the specified areas of the thumbnails are selected, sequentially in the partial display areas 108 to 111 displaying no medical image (e.g., in order of the partial display areas 108→110→109→111). In this case, in the above-described example, the medical image corresponding to the lung-field region 123 in the thumbnail 103 is arranged in the partial display area 108, and the medical image corresponding to the soft region 601 of the thumbnail 600 is arranged in the partial display area 110.

If another medical image has been already displayed in all of the partial display areas 108 to 111 in the main display area 102, the display processing unit 45 deletes a medical image that is being displayed in a predetermined partial display area (e.g., the partial display area 108, etc.), from the display screen. Then, the display processing unit 45 displays the medical image according to the selection instruction, in the partial display area that has become a blank space.

According to another example, the display processing unit 45 may delete a medical image whose display was started at the earliest point in time. According to another example, the display unit 36 may delete a medical image that was subjected to processing according to a user operation at the earliest point in time.

Returning to FIG. 14, after step S1407, the process in step S1408 is performed in which the control unit 37 judges whether or not an instruction to end the interpretation has been accepted from the user. If an instruction to end the interpretation has been accepted (Yes in step S1408), the control unit 37 ends the display processing. On the other hand, if an instruction to end the interpretation has not been accepted (No in step S1408), the control unit 37 advances the procedure to step S1406.

As described above, with the image display apparatus 10 according to the fourth embodiment, one thumbnail is generated for a data set including a plurality of medical images. Accordingly, the number of thumbnails displayed can be reduced, and the user's burden when selecting the thumbnail is reduced. Furthermore, since a plurality of specified areas can be set for one thumbnail, the image display apparatus 10 can display different medical images in response to input to different positions in one thumbnail. In this manner, the image display apparatus 10 can make it possible to search for a medical image with a simple user operation, while reducing the number of thumbnails.

Accordingly, with the image display apparatus according to the fourth embodiment, the following effects are obtained.

That is to say, a common thumbnail is generated for a data set including a plurality of medical images, so that the number of thumbnails can be reduced. Even with a common thumbnail, different medical images can be displayed according to a specified area selected. Accordingly, it is possible to display a freely selected image without increasing the user effort, while reducing the number of thumbnails.

First Modified Example

Figure 16A:
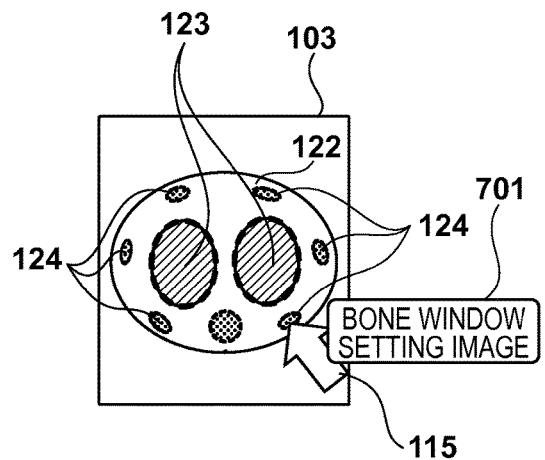
FIGS. 16A and 16B are explanatory diagrams of a first modified example.
Figure 16B:
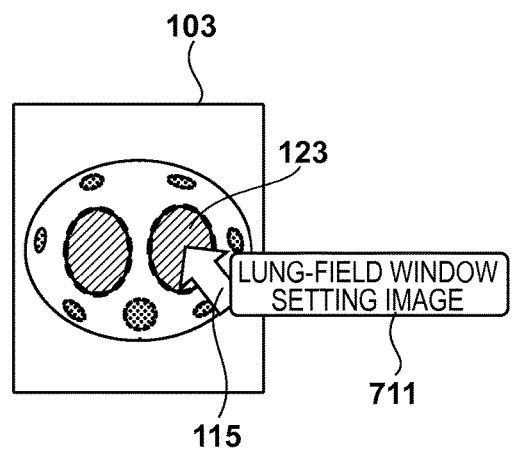

Next, a first modified example of the image display apparatus 10 according to the fourth embodiment will be described. In the first modified example, as shown in FIGS. 16A and 16B, if user input is currently positioned on a specified area in the thumbnail, the display processing unit 45 may display information indicating the specified area. In the example shown in FIG. 16A, the pointer 115 is positioned on the bone region 124. In this case, a character string 701 "bone window setting image" is displayed corresponding to the bone region 124. Furthermore, in the example shown in FIG. 16B, the pointer 115 is positioned on the lung-field region 123. In this case, a character string 711 "lung-field window setting image" is displayed corresponding to the lung-field region 123. Note that the information indicating a specified area is not limited to those in this embodiment, and it may be, for example, an icon indicating the specified area.

According to another example, in the case of including a loudspeaker, the image display apparatus 10 may output voice indicating the specified area (output processing).

Second Modified Example

Note that the data set setting condition is not limited to that in the embodiment described above. According to another example, the setting condition may be "the same examination date" (of the same patient). It is assumed that a breast CT image examination, a bone mineral density examination, and a perfusion scintigraphy examination are performed on one patient on the same day, and, in the breast CT image examination, a lung-field window setting image and a mediastinal window setting image are generated from one piece of projection data.

In this case, in step S1401, the data set setting unit 51 selects the lung-field window setting image and the mediastinal window setting image of the CT image, the bone mineral density examination data, and the myocardial perfusion scintigraphy examination data, and sets these pieces of data as a data set. It is assumed that, if a data set includes medical images captured by different image capturing modalities as shown in this example, the priority order between the modalities is set in advance in the storage unit 34 or the like.

In step S1402, the main image selecting unit 52 selects a main image, according to the priority order set in advance. In this example, the lung-field window setting image of the CT image data having the most detailed anatomical information, among the four medical images, is selected as a main image.

Next, in step S1403, the specified area extracting unit 53 extracts specified areas. In the case of using the specified area table shown in Table 3, "lung-field" corresponding to the lung-field window setting image, "soft region" corresponding to the mediastinal window setting image, "bone" corresponding to the bone mineral density examination data, and "heart" corresponding to the myocardial perfusion scintigraphy examination are extracted as specified areas.

Figure 17:
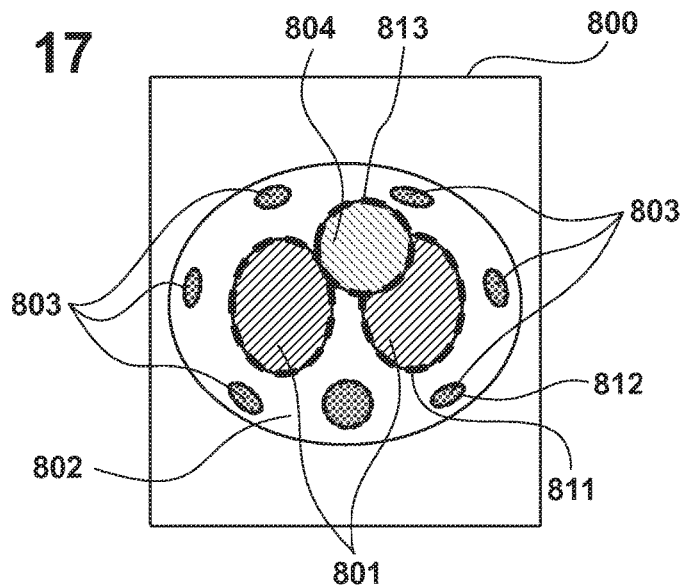
FIG. 17 is a diagram showing a thumbnail according to a second modified example.

For example, as shown in FIG. 17, a thumbnail 800 includes lung-field regions 801, a soft region 802, bone regions 803, and a heart region 804, and dividing lines 811 to 813 are drawn at the boundary positions between the regions.

Figure 18:
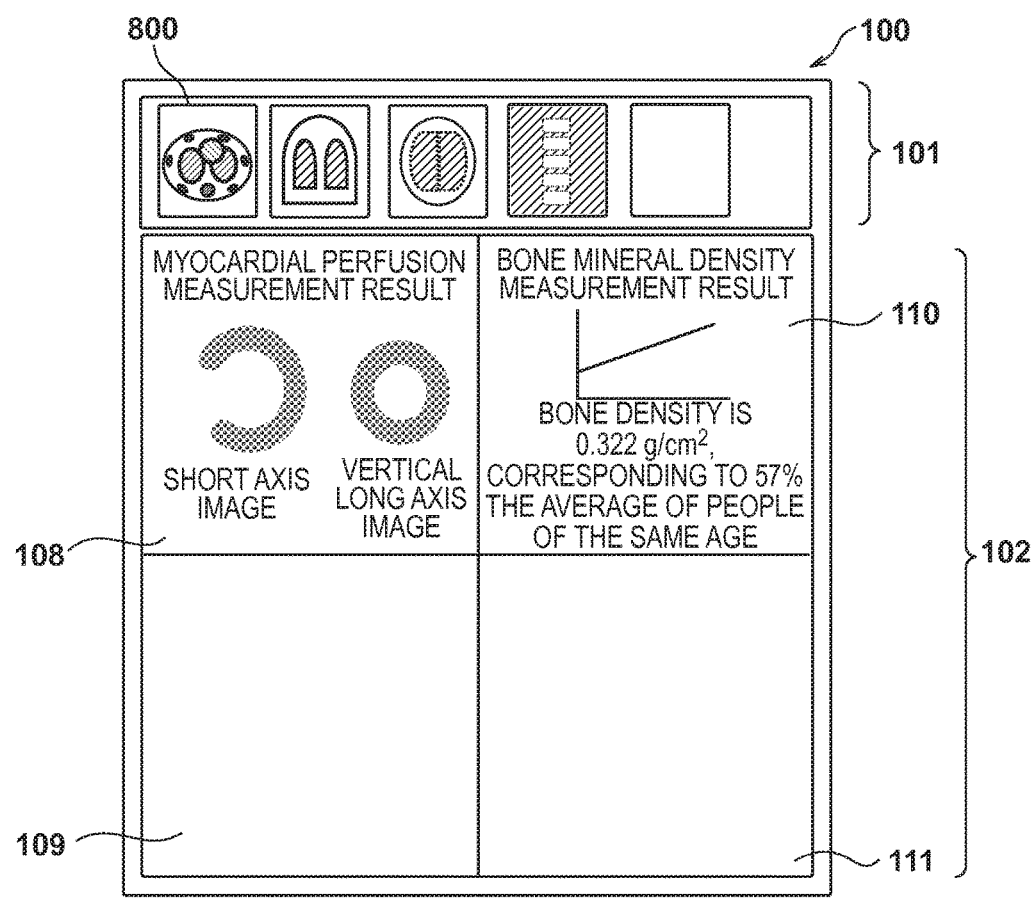
FIG. 18 is a diagram showing a display screen according to the second modified example.

In step S1406, if the heart region 804 of the thumbnail 800 is selected, the myocardial scintigraphy examination data is displayed in the partial display area 108 as shown in FIG. 18. If the bone region 803 is selected, the bone mineral density examination data is displayed in the partial display area 110.

According to another example, in a work station of the image capturing apparatuses, a radiological technologist or the like may perform image processing on a specific medical image, thereby generating another medical image. Examples of such another medical image include volume rendering image data of blood vessel data generated from lung CT image data, and the like. Also in this case, the specified area extracting unit 53 sets a lung-field window setting image as a main image, and extracts a lung-field region and a blood vessel region as specified areas, thereby generating a thumbnail in which the lung-field window setting image and the volume rendering image are taken as a data set.

Third Modified Example

The specified area extracting unit 53 may associate a plurality of medical images with one specified area. For example, it is assumed that a data set includes a lung-field window setting image, a mediastinal window setting image, and a bone window setting image, and each of the three images has an axial tomographic image, a coronal tomographic image, and a sagittal tomographic image. In this case, the data set includes nine medical images. Each tomographic image data is generated using a commonly known method in which three-dimensionally collected image data is reconstructed as a tomographic image in a freely selected direction and displayed (MPR: multi-planar reconstruction).

FIG. 19 is a diagram showing a display example of the display screen 100 according to this example. It is assumed that the axial tomographic image of the lung-field window setting image is selected as a main image. The thumbnail generated in this case is similar to the thumbnail 103 shown in FIG. 3B. That is to say, the thumbnail 103 includes the lung-field regions 123, the soft region 122, and the bone regions 124.

In this example, the specified area extracting unit 53 stores the axial tomographic image, the coronal tomographic image, and the sagittal tomographic image of the lung-field window setting image in association with the lung-field regions 123. Furthermore, the specified area extracting unit 53 stores the axial tomographic image, the coronal tomographic image, and the sagittal tomographic image of the mediastinal window setting image in association with the soft region 122. Furthermore, the specified area extracting unit 53 stores the axial tomographic image, the coronal tomographic image, and the sagittal tomographic image of the bone window setting image in association with the bone regions 124.

If the lung-field region 123 in the thumbnail 103 is selected, the axial tomographic image of the lung-field window setting image, corresponding to the lung-field region 123, is displayed in the partial display area 108 in the main display area 102 as shown in FIG. 19. Furthermore, the coronal tomographic image of the lung-field window setting image is displayed in the partial display area 110, and the sagittal tomographic image of the lung-field window setting image is displayed in the partial display area 109. If the bone region 124 in the thumbnail 103 is selected, the axial tomographic image, the coronal tomographic image, and the sagittal tomographic image of the bone window setting image, corresponding to the bone region 124, are displayed in the partial display areas in the main display area 102.

According to another example, it is assumed that one data set includes medical images captured by different modalities. In this case, the specified area extracting unit 53 associates the plurality of medical images captured by the different modalities with one specified area.

For example, it is assumed that a data set includes a lung-field window setting image captured by a breast region X-ray CT apparatus, bone scintigraphy examination data captured by a bone scintigraphy examination, and bone mineral density examination data captured by a bone mineral density examination. In this case, the lung-field window setting image is selected as a main image, and the thumbnail includes the lung-field region and the bone region. It is assumed that the lung-field window setting image is stored in association with the lung-field region, and the bone scintigraphy examination data and the bone mineral density examination data are stored in association with the bone region. In this case, if the bone region is selected by the user, the display processing unit 45 displays the bone scintigraphy examination data and the bone mineral density examination data, in different partial display areas in the main display area 102.

This modified example can be applied also to the case in which the same examinations are performed in a certain period of time, or to the case in which a contrast CT examination and a non-contrast CT examination are performed. For example, it is assumed that a data set includes a lung-field window setting image, a mediastinal window setting image, and a bone window setting image at each of two points in time consisting of a time A and a time B. In this case, the thumbnail includes the lung-field region, the soft region, and the bone region. The lung-field window setting images respectively at the time A and the time B are associated with the lung-field region, the mediastinal window setting images respectively at the time A and the time B are associated with the soft region, and the bone window setting images respectively at the time A and the time B are associated with the bone region.

If the lung-field region is selected by the user, the display processing unit 45 displays the lung-field window setting image at the time A and the lung-field window setting image at the time B, in different partial display areas in the main display area 102.

Fourth Modified Example

In the case where a plurality of medical images correspond to one specified area as in the third modified example, the control unit 37 may perform different types of image processing on the plurality of medical images corresponding to the specified area, according to different user operations on the specified area. For example, the control unit 37 may perform known subtraction processing as image processing corresponding to one user operation, thereby generating difference image data between a plurality of medical images. In this case, the difference image is displayed in the main display area 102.

As an example of image processing corresponding to another user operation, the control unit 37 may perform known alignment processing and overlapping processing on a plurality of medical images corresponding to one specified area, thereby generating and displaying an overlapping image of the plurality of medical images.

Note that examples of the different user operations include input methods such as double-click and right-click using a mouse or the like. Furthermore, in the case of operations on a touchscreen, examples thereof include input methods such as pinch-in, pinch-out, double-tapping, and the like.

Fifth Modified Example

The thumbnail generation unit 54 may fuse a plurality of main images, thereby generating a thumbnail. For example, it is assumed that a contrast CT examination and a non-contrast CT examination (plain CT examination) are performed on the same day, and a lung-field window setting image, a mediastinal window setting image data, and a bone window setting image are generated from each examination. In this case, the main image selecting unit 52 selects two medical images consisting of the lung-field window setting image in the contrast CT examination and the lung-field window setting image in the non-contrast CT examination, as main images.

The thumbnail generation unit 54 generates the left half area of the representative image based on the lung-field window setting image obtained by the contrast examination, and generates the right half area of the representative image based on the lung-field window setting image obtained from the non-contrast examination data. At that time, the thumbnail generation unit 54 can generate a natural corresponding image data by combining the two lung-field window setting images such that their slice positions are matched.

FIG. 20 is a diagram showing an exemplary thumbnail according to the fifth modified example. A thumbnail 1100 in FIG. 20 has a first area 1101 and a second area 1102. The first area 1101 is an area generated based on the lung-field window setting image obtained from the contrast examination data, and the second area is an area generated based on the lung-field window setting image obtained from the non-contrast examination data. A dividing line 1120 is shown between the first area 1101 and the second area 1102. Note that the dividing line 1120 may not be drawn in the thumbnail 1100.

It is assumed that a specified area 1111 is selected in the thumbnail 1100. In this case, the display processing unit 45 selects the lung-field window setting image obtained from the contrast examination data, corresponding to the specified area 1111, and displays it in the main display area 102. Furthermore, it is assumed that a specified area 1112 is selected. In this case, the display processing unit 45 selects the lung-field window setting image obtained from the non-contrast examination data, corresponding to the specified area 1112, and displays it in the main display area 102.

According to another example, it is assumed that a lung-field window setting image, a mediastinal window setting image data, and a bone window setting image at two points in time consisting of a time A and a time B are generated. In this case, the main image selecting unit 52 selects the lung-field window setting image at each point in time, as a main image. The thumbnail generation unit 54 generates the left half of the thumbnail from the lung-field window setting image obtained by the examination at the time A, and generates the right half from the lung-field window setting image obtained by the examination at the time B.

In this modified example, the thumbnail generation unit 54 fuses boundary faces of image data respectively corresponding to a plurality of main images simply at their center such that the slice positions of the main images are matched. Note that the method for fusing the boundary faces is not limited to those in this embodiment. For example, the thumbnail generation unit 54 may fuse boundary faces, using a known deformation and positioning method such as the free-form deformation method.

The thumbnail generation unit 54 may generate a new fused image based on a plurality of main images, and generate a thumbnail from that fused image. For example, the thumbnail generation unit 54 may perform known subtraction processing on a plurality of main images, thereby generating a difference image, and set the difference image as a thumbnail.

According to another example, the thumbnail generation unit 54 may perform known alignment processing and overlapping processing on a plurality of main images, and set the obtained image as a thumbnail.

If a new fused image, such as a difference image or an image obtained by overlapping processing, is generated in this manner, the specified area extracting unit 53 extracts specified areas (partial areas) from the new fused image.

Sixth Modified Example

The user may select a dividing line between specified areas instead of a specified area in step S1406, in the thumbnail displayed in step S1405. In this case, the instruction acceptance unit 55 accepts a selection instruction on each of the plurality of specified areas in contact with the dividing line. The display processing unit 45 specifies medical images respectively corresponding to the plurality of specified areas according to the selection instruction, and displays the specified medical images in the main display area 102.

Figure 21A:
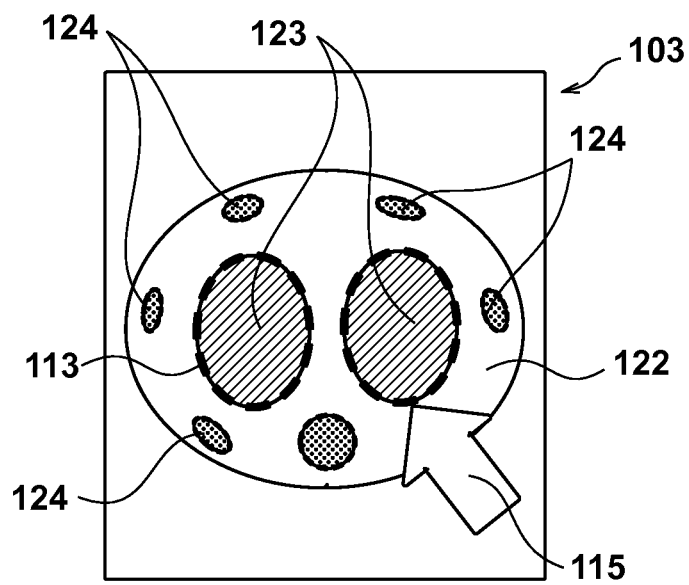
FIGS. 21A and 21B are explanatory diagrams of a sixth modified example.

For example, it is assumed that, as shown in FIG. 21A, the dividing line 113 is selected in the thumbnail 103 shown in FIG. 3B. In this case, the instruction acceptance unit 55 accepts a selection instruction on areas in contact with the dividing line 113, that is, the lung-field region 123 and the soft region 122.

Figure 21B:
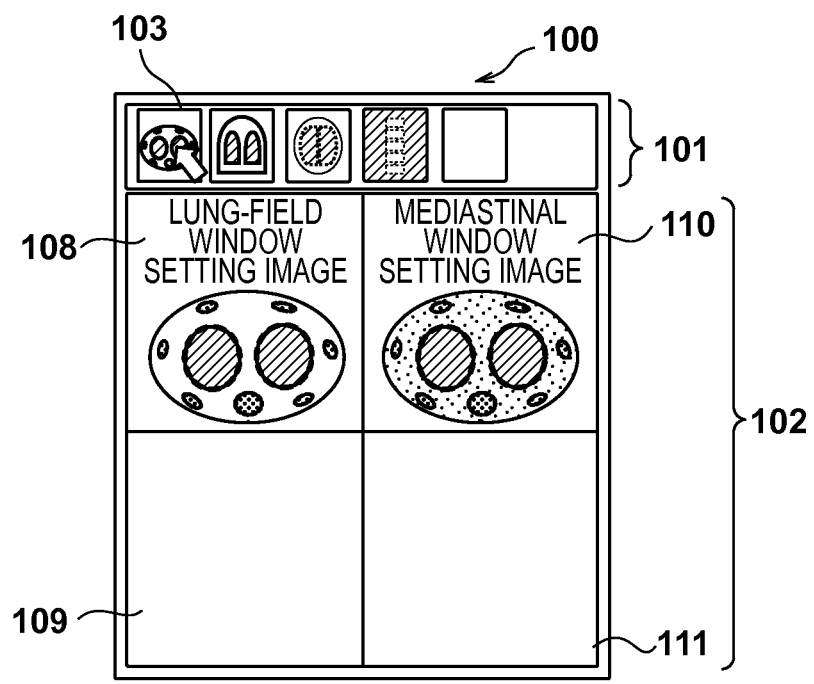

The display processing unit 45 specifies medical images respectively corresponding to the lung-field region 123 and the soft region 122, that is, the lung-field window setting image and the mediastinal window setting image, and displays these medical images in the main display area 102. FIG. 21B is a diagram showing a display example of medical images. In this manner, the lung-field window setting image is displayed in the partial display area 108, and the mediastinal window setting image is displayed in the partial display area 110.

Note that the user operation for displaying medical images is not limited to those in this embodiment. According to another example, the user may perform input across a plurality of specified areas, that is, perform input that extends over a dividing line. Also in this case, medical images respectively corresponding to the plurality of specified areas according to the input are displayed.

Seventh Modified Example

If a dividing line is selected by the user as described in the sixth modified example, the display processing unit 45 may perform image processing on medical images respectively corresponding to the plurality of specified areas in contact with the dividing line. For example, the display processing unit 45 may perform known subtraction processing on a plurality of medical images specified by a dividing line, thereby generating a difference image of the plurality of medical images. In this case, the display processing unit 45 displays the difference image, in the main display area 102.

According to another example, the display processing unit 45 may perform known alignment processing and overlapping processing, thereby generating an overlapping image of the plurality of medical images corresponding to the plurality of specified areas in contact with the dividing line. In this case, the display processing unit 45 displays the overlapping image, in the main display area 102.

Figure 22:
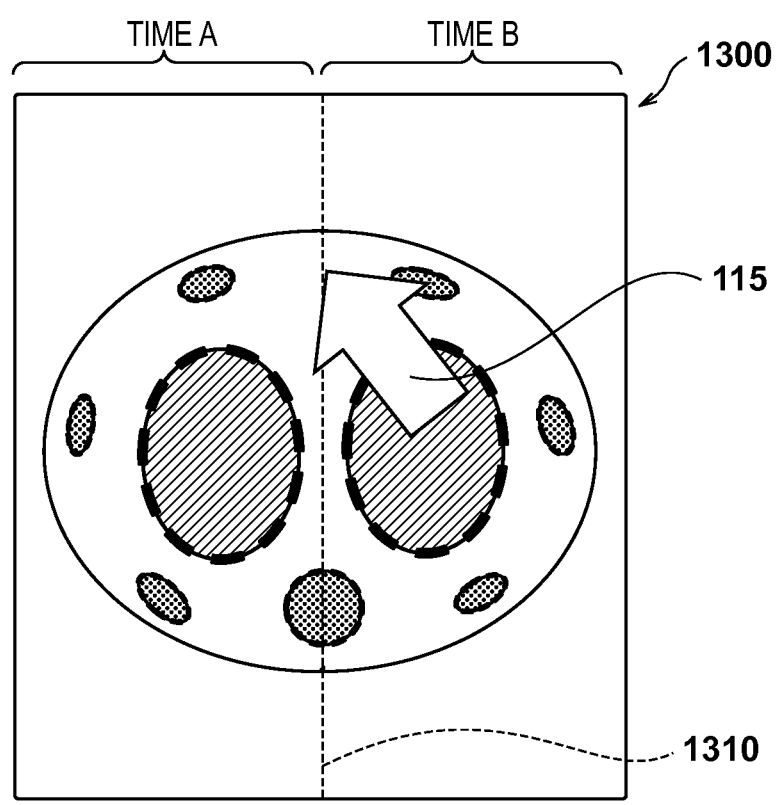
FIG. 22 is a diagram showing an exemplary thumbnail according to a seventh modified example.

Above, medical images in contact with a dividing line that divides anatomical areas are used as a plurality of medical images on which image processing is to be performed, but there is no limitation to this. For example, a boundary line between a plurality of main images in a thumbnail obtained by fusing the main images as shown in Modified Example 5 may be used. FIG. 22 is a diagram showing an exemplary thumbnail obtained by fusing a plurality of main images as shown in Modified Example 5. A thumbnail 1300 shown in FIG. 22 has an area generated based on a medical image obtained at a time A and an area generated based on a medical image obtained at a time B. It is assumed that the user selects a dividing line 1310 while viewing the position with the pointer 115 in the thumbnail 1300.

Figure 23A:
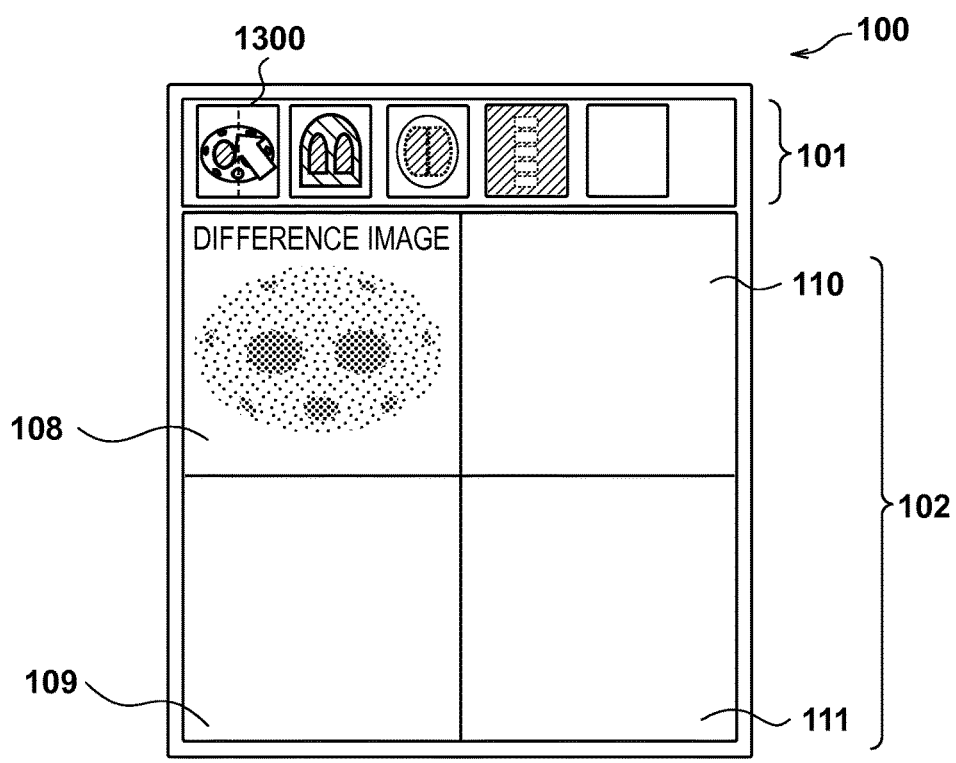
FIGS. 23A and 23B are diagrams showing display examples of difference images.

In this case, the display processing unit 45 performs known subtraction processing on the lung-field window setting image at the time A and the lung-field window setting image at the time B, thereby generating a difference image. The display processing unit 45 displays the difference image, in the main display area 102. FIG. 23A is a diagram showing a display example of the difference image. In FIG. 23A, the difference image is displayed in the partial display area 108.

Figure 23B:
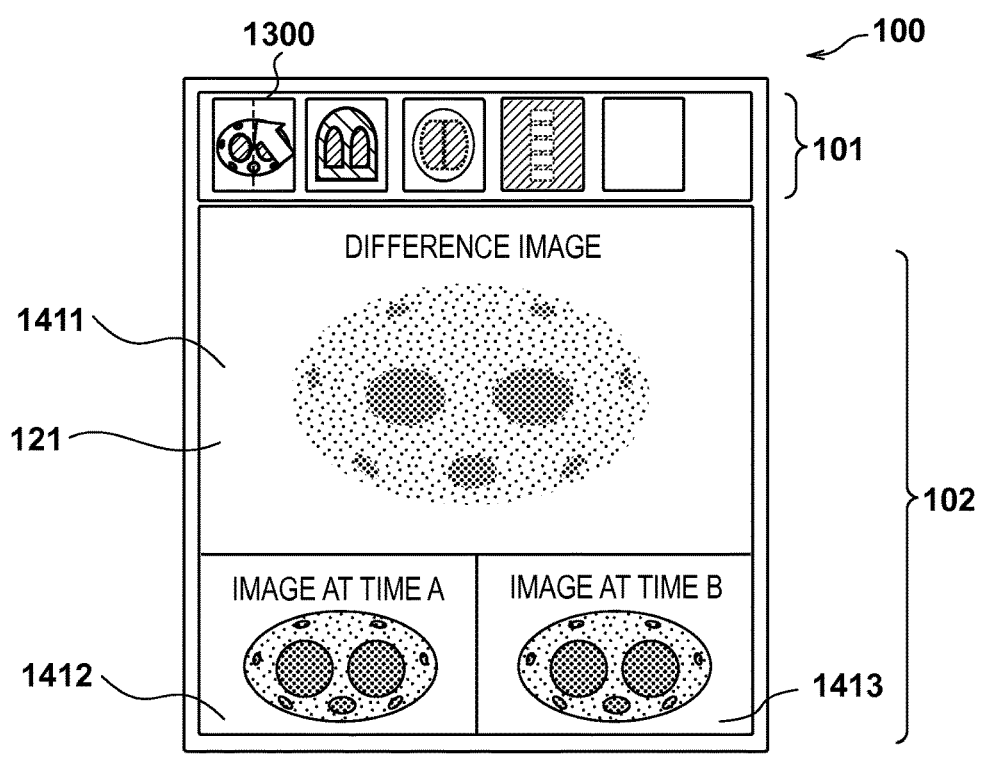

According to another example, the display processing unit 45 divides the main display area 102 into partial areas having different sizes as shown in FIG. 23B, and displays the difference image in a partial display area 1411 having the largest size. The display processing unit 45 may display medical images from which the difference image was generated, that is, the medical images respectively at the times A and B, in partial display areas 1412 and 1413 having smaller sizes. Note that processing that is to be performed on medical images in contact with a dividing line is not limited to those in this embodiment.

Eighth Modified Example

If a dividing line is selected as described in the sixth and seventh modified examples, the display processing unit 45 may display types of image processing that can be performed on medical images specified by the dividing line. Accordingly, the user can select desired image processing from among the displayed types of image processing.

FIG. 24 is a diagram showing a display example of an image processing selection window indicating types of image processing. It is assumed that the user selects the dividing line 113 while viewing the position with the pointer 115 in the thumbnail 103. In this case, the display processing unit 45 specifies types of image processing that can be performed on medical images respectively corresponding to the lung-field region 123 and the soft region 122 in contact with the dividing line 113. The display processing unit 45 displays an image processing selection window 1510 indicating the specified types of image processing. It is assumed that the types of image processing that can be performed on medical images divided along a dividing line are set in advance in the storage unit 34 or the like according to types of medical images.

If desired image processing is selected by the user, the instruction acceptance unit 55 accepts a selection instruction of the image processing. The control unit 37 performs the image processing according to the selection instruction, and displays the processing result.

According to another example, the control unit 37 may display predetermined types of image processing, in an image processing selection window, without judging whether or not the image processing can be performed on medical images divided along a dividing line.

Note that the method for designating types of image processing is not limited to the above-described method using the image processing selection window 1510. For example, the storage unit 34 or the like may store an image processing table for associating a type of input operation on a dividing line and a type of image processing. The control unit 37 refers to the image processing table, and specifies the type of image processing according to the type of input operation on a dividing line. For example, the control unit 37 performs simultaneous display, if right-click is input on a dividing line, and generates difference image data, if double-click is input. Note that the selecting methods of a processing content and the processing methods displayed in a window are not limited to those in this embodiment.

Ninth Modified Example

A configuration is possible in which the image display apparatus 10 can accept a selection instruction on a specified area, and an arrangement instruction designating an area in which a medical image corresponding to the selected specified area is to be arranged among the partial display areas 108 to 111, according to a series of user operations. The arrangement instruction is information designating arrangement to a position for displaying a medical image that is to be displayed, in the main display area 102, that is, from among the partial display areas of the medical image. In the arrangement instruction according to this example, the partial display areas 108 to 111 for displaying a medical image that is to be displayed are designated as positions for displaying a medical image.

For example, it is assumed that the user performs a drag-and-drop operation from a specified area to a partial area. More specifically, the user moves a mouse onto a specified area, further moves (drags) the mouse onto an arrangement target partial area in the state of selecting the specified area, and releases (drops) the mouse. In this case, the instruction acceptance unit 55 accepts a selection instruction on the specified area according to the user operation, and an arrangement instruction on the partial area (partial display area in which release (drop) was performed) according to the user operation. The display processing unit 45 arranges and displays the medical image that is to be displayed, in the partial display area according to the arrangement instruction.

Tenth Modified Example

The image display apparatus 10 accepts a selection instruction on a specified area and an arrangement instruction on a partial area according to user operations. Furthermore, in the image display apparatus 10 according to this example, the number of divided areas in the main display area 102 varies, and, each time a specified area is selected, the image display apparatus 10 specifies the number of divided areas and their positions, and specifies a divided area according to the arrangement instruction.

Figure 25:
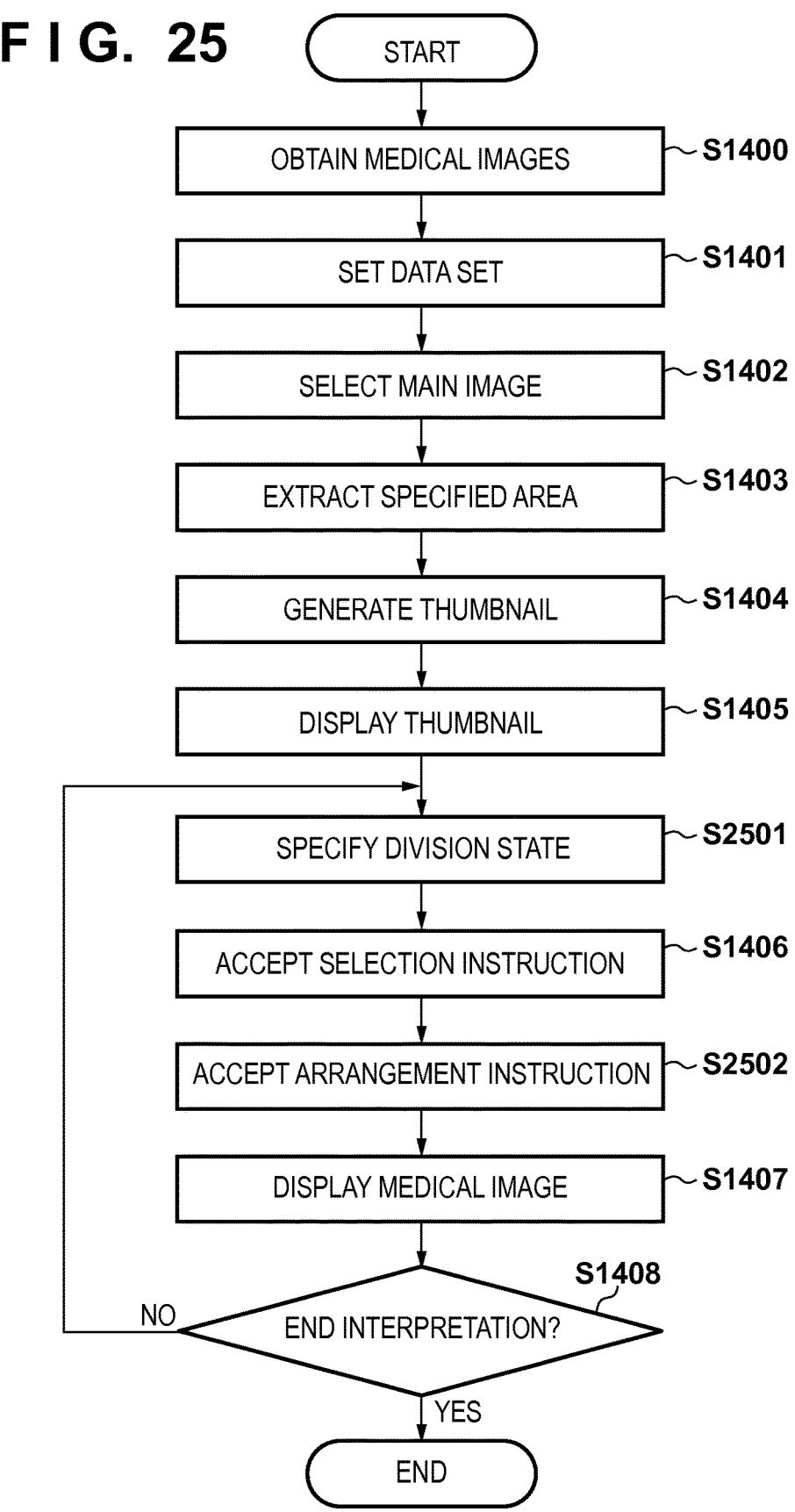
FIG. 25 is a flowchart illustrating image display processing according to a tenth modified example.

FIG. 25 is a flowchart illustrating image display processing according to the tenth modified example. Hereinafter, only steps different from those in the image display processing described in the foregoing embodiments will be described. Note that the same steps as those in the image display processing described in the foregoing embodiments are denoted by the same reference numerals.

After displaying the thumbnail in step S1405, the control unit 37 advances the procedure to step S2501. In step S2501, the control unit 37 specifies a division state of the main display area 102, and, then, advances the procedure to step S1406. The division state is expressed by the number of areas obtained by the division and the arrangement rule of the partial areas. For example, if the number of areas obtained by the division in the main display area 102 is taken as l, the number of rows is taken as n, and the number of columns is taken as m, the division state of the main display area 102 shown in FIG. 23A is (l, n, m)=(4, 2, 2). The division state may be any information as long as it indicates areas into which a medical image area is divided, and a specific content thereof is not limited to those in this example.

In step S1406, the control unit 37 accepts a selection instruction. If a user operation that drags a specified area in a certain direction is performed, in step S2502, the control unit 37 accepts input of an arrangement instruction in response to this operation. Note that the user operation corresponding to an arrangement instruction is not limited to those in this example.

According to another example, it is assumed that the image display apparatus 10 has a touchscreen monitor integrally provided with the operation unit 35 and the display unit 36. In this case, if the user performs an operation method commonly referred to as flick in a certain direction, the control unit 37 accepts input of an arrangement instruction in response to this operation.

The method for specifying a partial display area in which a medical image is to be arranged, from the direction designated by dragging or flicking is as described with reference to FIG. 11. That is to say, as shown in FIG. 11, the control unit 37 associates the partial display areas 108, 109, 110, and 111, respectively with angle ranges of 90° to 180°, 180° to 270°, 0° to 90°, and 270° to 0°. Upon accepting a user operation in a direction within an angle range of 90° to 180°, the control unit 37 accepts input of an arrangement instruction in the partial display area 108.

In a similar manner, upon accepting a user operation in a direction within an angle range of 0° to 90°, the control unit 37 accepts input of an arrangement instruction in the partial area 110. Furthermore, upon accepting a user operation in a direction within angle ranges of 180° to 270° and 270° to 0°, the control unit 37 accepts input of an arrangement instruction respectively in the partial areas 109 and 111.

As described above, in this example, the image display apparatus 10 can display a medical image targeted by the user, in a partial area targeted by the user. That is to say, it is possible to display an intended medical image in a targeted partial area, with less user effort.

Eleventh Modified Example

The image display apparatus 10 may not include the display unit 36. In this case, the image display apparatus 10 functions as a display control apparatus having the functions of the control unit 37 described in the foregoing embodiments, and may output an image that is to be displayed on the display unit 36, to an external display apparatus.

Other Embodiments

Part or the whole of the processing of the image display apparatus 10 according to the foregoing embodiments may be realized by a plurality of apparatuses via a network such as cloud.

As described above, according to the foregoing embodiments, medical images intended by a user can be displayed without complicated operations by the user.

Embodiments of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiments and/or that includes one or more circuits (e.g., application specific integrated circuit (ASIC)) for performing the functions of one or more of the above-described embodiments, and by a method performed by the computer of the system or apparatus by, for example, reading out and executing the computer executable instructions from the storage medium to perform the functions of one or more of the above-described embodiments and/or controlling the one or more circuits to perform the functions of one or more of the above-described embodiments. The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application Nos. 2014-120844 and 2014-120582, filed Jun. 11, 2014, which are hereby incorporated by reference herein in their entirety.

What is claimed is:

1. A display control apparatus for displaying a medical image, comprising:
   at least one processor; and
   at least one memory storing a program including instructions to be executed by the at least one processor to perform a method comprising:
   generating a thumbnail, using medical image data;
   setting partial areas in the thumbnail; and
   displaying a medical image, on a display unit, in response to an instruction to select the thumbnail that is displayed;
   wherein the displaying includes determining a display content of the medical image that is to be displayed on the display unit, based on a partial area specified by the instruction from the set partial areas,
   wherein the setting includes setting the partial areas in the thumbnail, based on anatomical information obtained from the medical image data.

2. The apparatus according to claim 1,
   wherein the method further comprising:
   obtaining, in response to an instruction to select the thumbnail that is displayed, a display condition corresponding to the partial area specified by the instruction;
   wherein the displaying includes displaying the medical image on the display unit, using the obtained display condition, in response to the instruction.

3. The apparatus according to claim 2,
   wherein the display condition is a display condition for displaying properly an anatomical area corresponding to a partial area specified by the instruction.

4. The apparatus according to claim 2,
   wherein the display condition includes at least one of a tone conversion condition for displaying the medical image on the display unit, a rate of magnification and a center position when displaying the medical image on the display unit.

5. The apparatus according to claim 2,
   wherein the displaying includes displaying the medical image in one of a plurality of partial display areas for displaying a medical image, in response to the instruction.

6. The apparatus according to claim 5,
   wherein, in a case where the thumbnail is dragged and dropped onto one partial display area of the plurality of partial display areas, the displaying includes displaying the medical image in the one partial display area, using a display condition corresponding to a partial area specified by a starting position of the dragging.

7. The apparatus according to claim 5,
   wherein the displaying includes associating a plurality of divided areas obtained by dividing the thumbnail based on an arrangement of the plurality of partial display areas, with the plurality of partial display areas, and includes displaying the medical image in a partial display area associated with a divided area specified by the instruction among the plurality of partial display areas.

8. The apparatus according to claim 7,
   wherein the displaying includes drawing or overlaying a dividing line indicating a boundary between the divided areas, on the thumbnail.

9. The apparatus according to claim 5,
   wherein the displaying includes selecting one partial display area of the plurality of partial display areas, based on a direction in which the thumbnail is dragged or flicked, and includes displaying the medical image in the selected partial display area, using a display condition corresponding to a partial area specified by a starting position of the dragging or the flicking.

10. The apparatus according to claim 2,
    wherein the set partial areas are determined on the basis of a modality used to obtain the medical image data and/or scanned site of the medical image data.

11. The apparatus according to claim 2,
    wherein the displaying includes drawing or overlaying a dividing line indicating a boundary between the partial areas, on the thumbnail.

12. The apparatus according to claim 2,
wherein the display condition is determined based on a modality used to obtain the medical image data and an anatomical area corresponding to a partial area.

13. The apparatus according to claim 1,
wherein the generating includes generating a thumbnail from a main image data which is representative of a group of a plurality of medical image data, and
the displaying includes selecting a target image from the group of the plurality of medical image data, and displaying the target image on the display unit, based on a designated position in the thumbnail in an instruction.

14. The apparatus according to claim 1,
wherein the generating includes generating a thumbnail, using a slice image determined according to a number of anatomical regions extracted from the medical image data.

15. A display control apparatus, comprising:
at least one processor; and
at least one memory storing a program including instructions to be executed by the at least one processor to perform a method comprising:
selecting a main image data from a data set including a plurality of medical image data;
displaying a thumbnail of the selected main image data, on a display unit;
setting partial areas obtained from the medical image data, in the thumbnail;
accepting a selection instruction on the set partial areas; and
specifying the medical image data corresponding to a partial area according to the selection instruction;
wherein the displaying includes displaying a medical image, based on the specified medical image data, and
wherein the setting includes setting the partial areas in the thumbnail, based on anatomical information obtained from the medical image data.

16. The apparatus according to claim 15,
wherein the displaying includes displaying, on the display unit, a display screen having areas for respectively displaying the thumbnail and the medical image,
the accepting includes accepting an arrangement instruction in a display area of the medical image, for displaying the medical image corresponding to the partial area according to the selection instruction, and
the displaying includes displaying, on the display unit, the display screen on which the medical image is arranged in the display area of the medical image according to the arrangement instruction.

17. The apparatus according to claim 15,
wherein, in a case where the plurality of medical image data correspond to the partial area, the specifying includes specifying each of the plurality of medical image data, and
the displaying includes displaying each of the plurality of medical image data.

18. The apparatus according to claim 15, wherein the method further comprising:
extracting partial areas of the selected main image data; and
generating the thumbnail;
wherein the displaying includes displaying the generated thumbnail.

19. The apparatus according to claim 15,
wherein, in a case where a user selects a dividing line between a plurality of partial areas included in the selected main image data displayed on the display unit, the accepting includes accepting the selection instruction on each of the plurality of partial areas in contact with the dividing line, and
the specifying includes specifying the medical image data corresponding to the respective partial areas according to the selection instruction.

20. A display control method for a display control apparatus, comprising:
a generation step of generating a thumbnail, using medical image data;
a setting step of setting partial areas in the thumbnail; and
a display control step of displaying a medical image, on a display unit, in response to an instruction to select the thumbnail that is displayed;
wherein, in the display control step, a display content of the medical image that is to be displayed on the display unit is determined on the basis of a partial area specified by the instruction from the set partial areas, and
wherein the setting step includes setting the partial areas in the thumbnail, based on anatomical information obtained from the medical image data.

21. A non-transitory computer-readable storage medium storing a program for causing a computer to execute a display control method comprising:
a generation step of generating a thumbnail, using medical image data;
a setting step of setting partial areas in the thumbnail; and
a display control step of displaying a medical image, on a display unit, in response to an instruction to select the thumbnail that is displayed,
wherein, in the display control step, a display content of the medical image that is to be displayed on the display unit is determined on the basis of a partial area specified by the instruction from the set partial areas, and
wherein the setting step includes setting the partial areas in the thumbnail, based on anatomical information obtained from the medical image data.

22. A display control method for a display control apparatus, comprising:
a selection step of selecting a main image data from a data set including a plurality of medical image data;
a displaying step of displaying a thumbnail of the selected main image data, on a display unit;
a setting step of setting partial areas obtained from the medical image data, in the thumbnail;
a accepting step of accepting a selection instruction on the set partial areas; and
a specifying step of specifying the medical image data corresponding to a partial area according to the selection instruction;
wherein the displaying step includes displaying a medical image, based on the specified medical image data, and
wherein the setting step includes setting the partial areas in the thumbnail, based on anatomical information obtained from the medical image data.

23. A non-transitory computer-readable storage medium storing a program for causing a computer to execute a display control method comprising:
a selection step of selecting a main image data from a data set including a plurality of medical image data;
a displaying step of displaying a thumbnail of the selected main image data, on a display unit;
a setting step of setting partial areas obtained from the medical image data, in the thumbnail;
a accepting step of accepting a selection instruction on the set partial areas; and a specifying step of specifying the medical image data corresponding to a partial area according to the selection instruction;

wherein the displaying step includes displaying a medical image, based on the specified medical image data, and wherein the setting step includes setting the partial areas in the thumbnail, based on anatomical information obtained from the medical image data.

* * * * *